(12) United States Patent
Kopczynski et al.

(10) Patent No.: US 9,849,122 B2
(45) Date of Patent: Dec. 26, 2017

(54) COMBINATION THERAPY

(71) Applicant: Aerie Pharmaceuticals, Inc., Durham, NC (US)

(72) Inventors: Casey Kopczynski, Chapel Hill, NC (US); Cheng-Wen Lin, Raleigh, NC (US); Jill Marie Sturdivant, Chapel Hill, NC (US); Mitchell A. deLong, Chapel Hill, NC (US)

(73) Assignee: Aerie Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 15/142,461

(22) Filed: Apr. 29, 2016

(65) Prior Publication Data

US 2016/0243105 A1   Aug. 25, 2016

Related U.S. Application Data

(63) Continuation of application No. 14/213,940, filed on Mar. 14, 2014, now abandoned.

(60) Provisional application No. 61/787,883, filed on Mar. 15, 2013.

(51) Int. Cl.
| | | |
|---|---|---|
| *C07D 217/22* | (2006.01) | |
| *A61K 31/472* | (2006.01) | |
| *A61K 31/4725* | (2006.01) | |
| *C07D 409/12* | (2006.01) | |
| *A61K 31/557* | (2006.01) | |
| *A61K 31/5575* | (2006.01) | |
| *A61K 31/559* | (2006.01) | |
| *A61K 9/00* | (2006.01) | |
| *A61K 9/08* | (2006.01) | |
| *A61K 47/48* | (2006.01) | |

(52) U.S. Cl.
CPC .......... *A61K 31/472* (2013.01); *A61K 9/0048* (2013.01); *A61K 9/08* (2013.01); *A61K 31/4725* (2013.01); *A61K 31/557* (2013.01); *A61K 31/559* (2013.01); *A61K 31/5575* (2013.01); *A61K 47/481* (2013.01); *C07D 217/22* (2013.01); *C07D 409/12* (2013.01)

(58) Field of Classification Search
CPC ............................ C07D 217/22; C07D 409/12
See application file for complete search history.

(56) References Cited

U.S. PATENT DOCUMENTS

| | | |
|---|---|---|
| 4,146,637 A | 3/1979 | Metz et al. |
| 4,337,256 A | 6/1982 | Yasushi et al. |
| 4,456,757 A | 6/1984 | Hidaka et al. |
| 4,709,032 A | 11/1987 | Hidaka et al. |
| 4,911,928 A | 3/1990 | Wallach |
| 4,954,512 A | 9/1990 | Oguro et al. |
| 5,508,288 A | 4/1996 | Forbes et al. |
| 5,519,036 A | 5/1996 | Himmelsbach et al. |
| 5,770,759 A | 6/1998 | Ueno et al. |
| 5,798,380 A | 8/1998 | Kaufman et al. |
| 5,889,052 A | 3/1999 | Klimko et al. |
| 5,891,646 A | 4/1999 | Barak et al. |
| 5,977,173 A | 11/1999 | Wos et al. |
| 5,994,397 A | 11/1999 | Selliah et al. |
| 6,025,392 A | 2/2000 | Selliah et al. |
| 6,030,999 A | 2/2000 | Stjernschantz et al. |
| 6,037,364 A | 3/2000 | Burk |
| 6,037,368 A | 3/2000 | Selliah et al. |
| 6,048,895 A | 4/2000 | Wos et al. |
| 6,110,693 A | 8/2000 | Barak et al. |
| 6,110,912 A | 8/2000 | Kaufman et al. |
| 6,362,177 B1 | 3/2002 | Shiota et al. |
| 6,586,425 B2 | 7/2003 | Kaufman et al. |
| 6,699,891 B1 | 3/2004 | Kawanishi et al. |
| 6,787,534 B2 | 9/2004 | Haneda et al. |
| 7,268,143 B2 | 9/2007 | Jagtap et al. |
| 7,329,684 B2 | 2/2008 | Mjalli et al. |
| 7,345,158 B2 | 3/2008 | Egashira et al. |
| 7,361,678 B2 | 4/2008 | Mjalli et al. |
| 7,374,891 B2 | 5/2008 | Shahbaz |
| 7,378,498 B2 | 5/2008 | Worley et al. |
| 7,470,787 B2 | 12/2008 | deLong et al. |
| 7,671,205 B2 | 3/2010 | deLong et al. |
| 8,034,943 B2 | 10/2011 | deLong et al. |
| 8,129,411 B2 | 3/2012 | Ehara et al. |
| 8,357,699 B2 | 1/2013 | deLong et al. |
| 8,394,826 B2 | 3/2013 | deLong et al. |

(Continued)

FOREIGN PATENT DOCUMENTS

| | | |
|---|---|---|
| EP | 0109023 | 5/1984 |
| EP | 0232569 | 8/1987 |

(Continued)

OTHER PUBLICATIONS

Anonymous, "Aerie Pharmaceuticals, Inc. Gets Good News on Glaucoma Treatment" (Feb. 11, 2012) Retrieved from the Internet: URL:http://www.biospace.com.

Banker, G.S. et al., Modern Pharmaceutics, Marcel Dekker, Inc., New York, (1979) Chapters 9 and 10.

Berge et al, 1977, "Pharmaceutically Acceptable Salts." J. Pharm. Sci. vol. 66, pp. 1-19.

Bird, G.J. et al., "N-methyl as a bioisostere for the oxygen link between the aromatic rings of aryloxyphenoxypropionate herbicides," Bioorg. Med. Chem. Lett. (1997) 7:1489-1492.

(Continued)

*Primary Examiner* — James D. Anderson
(74) *Attorney, Agent, or Firm* — K&L Gates LLP; Louis C. Cullman; Benjamin D. Heuberger

(57) ABSTRACT

Described herein are compounds and compositions for treating glaucoma and/or reducing intraocular pressure. Compositions may comprise an isoquinoline compound and a prostaglandin or a prostaglandin analog. Compounds described herein include those in which an isoquinoline compound is covalently linked to a prostaglandin or a prostaglandin analog, and those in which an isoquinoline compound and a prostaglandin free acid together form a salt.

21 Claims, 2 Drawing Sheets

(56) References Cited

U.S. PATENT DOCUMENTS

| | | |
|---|---|---|
| 8,450,344 B2 | 5/2013 | deLong et al. |
| 8,455,513 B2 | 6/2013 | deLong et al. |
| 8,455,514 B2 | 6/2013 | deLong et al. |
| 8,455,647 B2 | 6/2013 | deLong et al. |
| 8,716,310 B2 | 5/2014 | deLong et al. |
| 8,759,388 B2 | 6/2014 | deLong et al. |
| 8,809,326 B2 | 8/2014 | Bosanac et al. |
| 8,871,757 B2 | 10/2014 | deLong et al. |
| 8,921,392 B2 | 12/2014 | deLong et al. |
| 9,096,569 B2 | 8/2015 | deLong et al. |
| 2004/0091946 A1 | 5/2004 | Oakley et al. |
| 2004/0176462 A1 | 9/2004 | Kawanishi et al. |
| 2005/0032125 A1 | 2/2005 | Oakley et al. |
| 2005/0176712 A1 | 8/2005 | Wakabayashi et al. |
| 2005/0245509 A1 | 11/2005 | Nakajima et al. |
| 2005/0282805 A1 | 12/2005 | Hangeland et al. |
| 2006/0270670 A1 | 11/2006 | Chew et al. |
| 2007/0111983 A1 | 5/2007 | Fong |
| 2007/0123561 A1 | 5/2007 | Lee et al. |
| 2007/0129404 A1 | 6/2007 | Hagihara et al. |
| 2007/0135499 A1 | 6/2007 | deLong et al. |
| 2007/0149473 A1 | 6/2007 | Chatterton et al. |
| 2007/0149548 A1 | 6/2007 | Hellberg et al. |
| 2007/0167444 A1 | 7/2007 | Kuramochi et al. |
| 2007/0238741 A1 | 10/2007 | Nagarathnam et al. |
| 2008/0021026 A1 | 1/2008 | Kahraman et al. |
| 2008/0021217 A1 | 1/2008 | Borchardt |
| 2008/0058384 A1 | 3/2008 | Lee et al. |
| 2008/0096238 A1 | 4/2008 | Sharif et al. |
| 2008/0125427 A1 | 5/2008 | Sehon et al. |
| 2008/0139595 A1 | 6/2008 | Schirok et al. |
| 2008/0153799 A1 | 6/2008 | Laurent et al. |
| 2008/0153813 A1 | 6/2008 | Chen et al. |
| 2008/0194584 A1 | 8/2008 | Birault et al. |
| 2008/0275029 A1 | 11/2008 | Berdini et al. |
| 2009/0005321 A1 | 1/2009 | Zimmer et al. |
| 2009/0069371 A1 | 3/2009 | deLong et al. |
| 2010/0093790 A1 | 4/2010 | deLong et al. |
| 2010/0105650 A1 | 4/2010 | Plettenburg et al. |
| 2011/0015204 A1 | 1/2011 | Bencsik et al. |
| 2012/0135984 A1 | 5/2012 | deLong et al. |
| 2014/0187617 A1 | 7/2014 | deLong et al. |
| 2014/0275160 A1 | 9/2014 | Kopczynski |
| 2014/0275161 A1 | 9/2014 | Kopczynski |
| 2014/0288086 A1 | 9/2014 | Cui et al. |
| 2014/0357652 A1 | 12/2014 | Bosanac et al. |
| 2015/0119419 A1 | 4/2015 | deLong et al. |
| 2015/0175549 A1 | 6/2015 | deLong et al. |
| 2015/0297581 A1 | 10/2015 | Bosanac et al. |
| 2015/0299159 A1 | 10/2015 | deLong et al. |
| 2016/0016951 A1 | 1/2016 | Schiemann et al. |
| 2016/0280656 A1 | 9/2016 | deLong et al. |

FOREIGN PATENT DOCUMENTS

| | | |
|---|---|---|
| EP | 0389995 | 10/1990 |
| EP | 0482939 | 4/1992 |
| EP | 1541151 | 6/2005 |
| EP | 1550660 | 7/2005 |
| JP | 2005227441 | 8/2005 |
| JP | 2007236388 | 9/2007 |
| JP | 2007246466 | 9/2007 |
| WO | WO 93/18028 | 9/1993 |
| WO | WO 95/19964 | 7/1995 |
| WO | WO 96/10407 | 4/1996 |
| WO | WO 97/23223 | 7/1997 |
| WO | WO 98/12175 | 3/1998 |
| WO | WO 98/20880 | 5/1998 |
| WO | WO 98/20881 | 5/1998 |
| WO | WO 98/21180 | 5/1998 |
| WO | WO 98/21181 | 5/1998 |
| WO | WO 98/21182 | 5/1998 |
| WO | WO 98/39293 | 9/1998 |
| WO | WO 98/50024 | 11/1998 |
| WO | WO 98/57930 | 12/1998 |
| WO | WO 98/57942 | 12/1998 |
| WO | WO 99/02165 | 1/1999 |
| WO | WO 99/12895 | 3/1999 |
| WO | WO 99/12896 | 3/1999 |
| WO | WO 99/12898 | 3/1999 |
| WO | WO 99/25358 | 5/1999 |
| WO | WO 99/26629 | 6/1999 |
| WO | WO 99/32441 | 7/1999 |
| WO | WO 00/03736 | 1/2000 |
| WO | WO 00/03980 | 1/2000 |
| WO | WO 2000/076970 | 12/2000 |
| WO | WO 2001/037826 | 5/2001 |
| WO | WO 01/47891 | 7/2001 |
| WO | WO 01/53268 | 7/2001 |
| WO | WO 01/53274 | 7/2001 |
| WO | WO 01/56607 | 8/2001 |
| WO | WO 02/22576 | 3/2002 |
| WO | WO 02/32864 | 4/2002 |
| WO | WO 02/085857 | 10/2002 |
| WO | WO 02/085859 | 10/2002 |
| WO | WO 03/064397 | 8/2003 |
| WO | WO 03/073999 | 9/2003 |
| WO | WO 03/080578 | 10/2003 |
| WO | WO 2004/029045 | 4/2004 |
| WO | WO 2004/078747 | 9/2004 |
| WO | WO 2005/020921 | 3/2005 |
| WO | WO 2005/035503 | 4/2005 |
| WO | WO 2005/037257 | 4/2005 |
| WO | WO 2006/041119 | 4/2006 |
| WO | WO 2006/051290 | 5/2006 |
| WO | WO 2006/062982 | 6/2006 |
| WO | WO 2006/076706 | 7/2006 |
| WO | WO 2007/008926 | 1/2007 |
| WO | WO 2007/008942 | 1/2007 |
| WO | WO 2007/060028 | 5/2007 |
| WO | WO 2007/065916 | 6/2007 |
| WO | WO 2007/076360 | 7/2007 |
| WO | WO 2007/076367 | 7/2007 |
| WO | WO 2007/100880 | 9/2007 |
| WO | WO 2007/142323 | 12/2007 |
| WO | WO 2008/011557 | 1/2008 |
| WO | WO 2008/011560 | 1/2008 |
| WO | WO 2008/016016 | 2/2008 |
| WO | WO 2008/036459 | 3/2008 |
| WO | WO 2008/036540 | 3/2008 |
| WO | WO 2008/049000 | 4/2008 |
| WO | WO 2008/049919 | 5/2008 |
| WO | WO 2008/054599 | 5/2008 |
| WO | WO 2008/077057 | 6/2008 |
| WO | WO 2008/077550 | 7/2008 |
| WO | WO 2008/077551 | 7/2008 |
| WO | WO 2008/077552 | 7/2008 |
| WO | WO 2008/077553 | 7/2008 |
| WO | WO 2008/077554 | 7/2008 |
| WO | WO 2008/077555 | 7/2008 |
| WO | WO 2008/077556 | 7/2008 |
| WO | WO 2008/079880 | 7/2008 |
| WO | WO 2008/079945 | 7/2008 |
| WO | WO 2008/086269 | 7/2008 |
| WO | WO 2008/124665 | 10/2008 |
| WO | WO 2009/091898 | 7/2009 |
| WO | WO 2010/011853 | 1/2010 |
| WO | WO 2010/126626 | 11/2010 |
| WO | WO 2010/127329 | 11/2010 |
| WO | WO 2010/127330 | 11/2010 |
| WO | WO 2012/105674 | 8/2012 |

OTHER PUBLICATIONS

Blough BE, Keverline KI, Nie Z, Navarro H, Kuhar MJ, Carroll FI (2002). "Synthesis and transporter binding properties of 3beta-[4'-(phenylalkyl, phenylalkenyl, and phenylalkynyl) phenyltropane]-2beta-carboxylic acid methyl esters: evidence of a remote phenyl binding domain on the dopamine transporter". J. Med. Chem. 45 (18): 4029-37.

C.T.F.A. Cosmetic Ingredient Handbook, "Surfactants—Emulsifying Agents", Second Edition, The Cosmetic, Toiletry, and Fragrance Association, New York, Wenninger, J.A. et al., eds. (1992) 587-592.

Calmes et al., Eur. J. Org. Chem. 2000, 2459-2466.

(56) References Cited

OTHER PUBLICATIONS

"Cancer", MedlinePlus (retrieved Jul. 6, 2007) 10 pages, http://www.nlm.nih.gov/medlineplus/cancer.html.
Capdeville, R. et al., "Glivec (STI571, IMATINIB), A Rationally Developed, Targeted Anticancer Drug", Nature Reviews Drug Discovery (2002) 1:493-502.
Chen, P. et al., "Identification of novel and potent isoquinoline aminooxazole-based IMPDH inhibitors," Bioorg. Med. Chem. Lett. (2003) 13(7):1345-1348.
Cheung, S.T. et al. Can. J. Chem. 1977, 55,906-910.
Dancey, J. et al., "Issues and Progress with Protein Kinase Inhibitors for Cancer Treatment", Nature Reviews Drug Discovery (2003) 2:296-313.
deLong et al., "Discovery and SAR of a Class of Ocularly-active Compounds Displaying a Dual Mechanism of Activity for the Treatment of Glaucoma" (May 6, 2012) Retreived from the Internet: URL:http://www.aeriepharma.com.
Dorwald, F.Z., Side Reactions in Organic Synthesis. A Guide to Successful Synthesis Design, Wiley-VCH, Weinheim (2005) IX of Preface and 1-15.
Dowton et al., "Influence of Liposomal Composition on Topical Delivery of Encapsulated Cyclosporin A", S.T.P. Pharma Sciences, vol. 3, pp. 404-407 (1993).
Foye, Foye's Principles of Medicinal Chemistry, 5th Edition (2002) Lippencott, Williams, Wilkins, p. 59-63.
Gingras et al., "In Synthesis and evaluation of 4-(1-aminoalkyl)-N-(4-pyridyl)-cyclohexanecarboxamides as Rho-kinase inhibitors and neurite outgrowth promoters," Bioorganic & Medicinal Chemistry Letters, 2004, vol. 14, pp. 4931-4934.
Golub, T.R. et al., "Molecular classification of cancer: class discovery and class prediction by gene expression monitoring," Science (1999) 286:531-537.
Hackam, A.S. et al., "The Wnt Signaling Pathway in Retinal Degenerations", IUBMB Life (2005) 57(6):381-388.
Hazeldine, S.T. et al., "II. Synthesis and biological evaluation of some bioisosteres and cogeners of the antitumour agent, 2{4[7-chloro-2-quinoxalinyl)oxy]phenoxy}propionic acid (XK469)," J. Med. Chem. (2002) 45:3130-3137.
He R, Kurome T, Giberson KM, Johnson KM, Kozikowski AP (2005). "Further structure-activity relationship studies of piperidine-based monoamine transporter inhibitors: effects of piperidine ring stereochemistry on potency. Identification of norepinephrine transporter selective ligands and broad-spectrum transporter inhibitors". J. Med. Chem. 48 (25): 7970-9.
Helal, C.J. et al., "Discovery and SAR of 2-aminothiazole inhibitors of cyclin-dependent kinase 5/p25 as a potential treatment for Alzheimer's disease," Bioorg. Med. Chem. (2004) 14(22):5521-5525.
Helzner, "Bright New Ideas in Glaucoma Treatment" (2013) Retreived from the Internet: URL:http://mydigimag.rrd.com.
Hu, E. et al., "Rho kinase as potential therapeutic target for cardiovascular diseases: opportunities and challenges," Exp. Opin. Ther. Targets (2005) 9:715-736.
Inouye, Y. et al., "The Absolute Configurations of TRANS-1,2-Cyclopropanedicarboxylic Acid and TRANS-2-Phenylcyclopropanecarboxylic Acid", Int'l. J. Org. Chem. (1964) 20(5):1695-1699.
Ito, N. et al., "A medium-term rat liver bioassay for rapid in vivo detection of carcinogenic potential of chemicals," Cancer Science, Jan. 2003, vol. 94, No. 1, pp. 3-8.
Jacobs, M. et al., "The structure of dimeric ROCK I reveals the mechanism for ligand selectivity," J. Bio. Chem., 2006, pp. 260-268, published on Jan. 6, 2006.
Karaman, M.W. et al., "A quantitative analysis of kinase inhibitor selectivity," Nature Biotech. (2008) 26(1):127-132.
Lala, P.K. et al., "Role of nitric oxide in tumor progression: lessons from experimental tumors," Cancer and Metastasis Reviews (1998) 17:91-106.

Liljebris, C. et al., "Derivatives of 17- Phenyl-18,19,20-trinorprostaglandin F2α Isopropyl Ester: Potential Antiglaucoma Agents," J. Med. Chem. (1995) 38(2):289-304.
Loge, C; Siomboing, X et al. J, of Enzy Inhib & Med Chem, 2003,18,127-128.
Matsui, T. et al., "Novel 5-HT3 antagonists. Isoquinolinones and 3-aryl-2-pyridones," J. Med. Chem. (1992) 35:3307-3319.
McCutcheon's, "Emulsifiers & Detergents", North American Edition (1994) vol. 1:236-239.
Meanwell, "Synopsis of some recent tactical application of bioisosteres in drug design," J. Med. Chem., 2011, vol. 54, pp. 2529-2591.
Nakanishi et al. FEBS Letters 368, (1995) 411-414.
Oakley, R.H. et al. "The Cellular Distribution of Fluorescently Labeled Arrestins Provides a Robust, Sensitive and Universal Assay for Screening G Protein-Coupled Receptors," Assay and Drug Development Technologies (2002) 1(1-1):21-30.
Olson, "Application for ROCK kinase inhibition," Current Opinion in Cell Biology, 2008, vol. 20, pp. 242-248.
Parang, K. et al., "Design strategies for protein kinase inhibitors," Curr. Opin. In Drug Disc. & Dev. (2004) 7(5):617-629.
Pardridge, "The Blood-Brain Barrier: Bottleneck in Brain Drug development," J. Am. Soc. Exper. NeuroTherapeutics, 2005, vol. 2, p. 3-14.
Penmetsa, K.V. et al., "Development of Reversed-Phase Chiral HPLC Methods Using Mass Spectrometry Compatible Mobile Phases", J. Liquid Chroma. Rel. Tech. (2000) 23(6-10):831-839.
Penn, R.B. et al., "Pharmacological Inhibition of Protein Kinases in Intact Cells: Antagonism of Beta Adrenergic Receptor Ligand Binding by H-89 Reveals Limitations of Usefulness." J. Pharm. Exp. Ther. (1999) 288(2):428-437.
Pharmasolve (N-Methyl-2-Pyrrolidone) product spcification, International Specialty Products, 2000, 10 pages.
Rashid et al., "Development of Rho-kinase inhibitors for cardiovascular medicine," Trends in Pharmacological Science, 2007, vol. 28, pp. 296-302.
Shankar, G. et al., "Protein-kinase-specific inhibitors block Langerhans' cell migration by inhibiting interleukin-1α release", Immunology (1999) 96:230-235.
Stirewalt, D.L. et al., "The Role of FLT3 in Haematopoietic Malignancies", Nature Reviews Cancer (2003) 3:650-665.
STN Registry Database entry for CAS RN 309903-43-6, Published in database Dec. 20, 2000.
Tamura, M., et al., "Development of specific Rho-kinase inhibitors and their clinical application," Biochimica et Biophysica Acta, 2005, vol. 1754, pp. 245-252.
Torres, G.E. et al. (2003). "Plasma membrane monoamine transporters: structure, regulation and function". Nat. Rev. Neurosci. 4 (1): 13-25.
Van Muijlwijk-Koezen et al., "A novel class of adenosine A3 receptor-ligands. 2. Structure affinity profile of a series of isoquinoline and quinazoline compounds," J. Med. Chem. (1998) 41:3994-4000.
Wallach and Philippot, "New Type of Lipid Vesicle: Novasome®", Liposome Technology, vol. 1, pp. 141-156 (1993).
Webster, F.X. et al., "Following the Course of Resolution of Carboxylic Acids by 13C NMR Spectrometry of Amine Salts" J. Org. Chem. (1982) 47(26):5225-5226.
West, A.R., "Solid state chemistry and its applications," Wiley, New York (1988) pp. 358 and 365.
Westaway, S.M. et al., "N-tetrahydroquinolinyl, N-quinolinyl and N-isoquinolinyl biaryl carboxamides as antagonists of TRPV1," Biorg. Med. Chem. Lett. (2006) 16:4533-4536.
Westra, J. et al., "p38 Mitogen-Activated Protein Kinase (MAPK) in Rheumatoid Arthritis", Mini-Reviews in Medicinal Chemistry (2006) 6(8):867-874.
Yamashita et al., "The therapeutic effects of Rho-Rock inhibitors on CNS disorder," Therapeutics and Clinical Risk Management, 2008, vol. 4, pp. 605-615.
United States Office Action for U.S. Appl. No. 11/485,182 dated Apr. 16, 2009 (13 pages).
United States Office Action for U.S. Appl. No. 12/274,887 dated Jun. 16, 2009 (11 pages).

(56) References Cited

OTHER PUBLICATIONS

United States Patent Office Action for U.S. Appl. No. 12/639,670 dated Jan. 31, 2011 (8 pages).
United States Patent Office Action for U.S. Appl. No. 12/639,670 dated Jul. 27, 2011 (5 pages).
United States Patent Office Action for U.S. Appl. No. 11/621,887 dated May 18, 2010 (8 pages).
United States Patent Office Action for U.S. Appl. No. 11/621,887 dated Oct. 29, 2010 (14 pages).
United States Patent Office Action for U.S. Appl. No. 13/017,708 dated Apr. 3, 2012 (11 pages).
United States Patent Office Notice of Allowance for U.S. Appl. No. 13/017,708 dated Sep. 17, 2012 (8 pages).
United States Patent Office Notice of Allowance for U.S. Appl. No. 13/017,708 dated Oct. 23, 2012 (7 pages).
United States Patent Office Notice of Allowability for U.S. Appl. No. 13/01,7708 dated Dec. 12, 2012 (5 pages).
United States Patent Office Notice of Allowance for U.S. Appl. No. 11/621,887 dated Feb. 27, 2013 (8 pages).
United States Patent Office Action for U.S. Appl. No. 13/723,811 dated Jan. 27, 2014 (8 pages).
United States Patent Office Action for U.S. Appl. No. 13/723,811 dated Jun. 17, 2014 (6 pages).
United States Patent Office Notice of Allowance for U.S. Appl. No. 13/723,811 dated Aug. 19, 2014 (11 pages).
United States Patent Office Action for U.S. Appl. No. 14/583,439 dated Jun. 23, 2015 (6 pages).
United States Patent Office Action for U.S. Appl. No. 14/583,439 dated Oct. 30, 2015 (7 pages).
United States Patent Office Notice of Allowance for U.S. Appl. No. 14/583,439 dated Feb. 12, 2016 (8 pages).
United States Office Action for U.S. Appl. No. 11/621,892 dated Aug. 8, 2008 (9 pages).
United States Office Action for U.S. Appl. No. 11/621,892 dated Mar. 9, 2009 (6 pages).
United States Patent Office Action for U.S. Appl. No. 12/701,963 dated May 10, 2011 (3 pages).
United States Patent Office Action for U.S. Appl. No. 13/230,105 dated Mar. 5, 2012 (8 pages).
United States Patent Office Final Rejection for U.S. Appl. No. 13/230,105 dated Jul. 9, 2012 (11 pages).
United States Patent Office Notice of Allowance for U.S. Appl. No. 13/230,105 dated Mar. 19, 2013 (5 pages).
United States Patent Office Action for U.S. Appl. No. 12/009,326 dated Feb. 3, 2011 (8 pages).
United States Patent Office Notice of Allowance for U.S. Appl. No. 12/009,326 dated Jan. 6, 2012 (5 pages).
United States Patent Office Notice of Allowance for U.S. Appl. No. 12/009,326 dated Feb. 25, 2013 (8 pages).
United States Patent Office Action for U.S. Appl. No. 12/704,822 dated Apr. 30, 2012 (34 pages).
United States Patent Office Final Rejection for U.S. Appl. No. 12/704,822 dated Jan. 16, 2013 (16 pages).
United States Patent Office Action for U.S. Appl. No. 12/704,822 dated Oct. 10, 2013 (11 pages).
United States Patent Office Action for U.S. Appl. No. 12/704,822 dated May 8, 2014 (13 pages).
United States Patent Office Notice of Allowance for U.S. Appl. No. 12/704,822 dated Sep. 9, 2014 (11 pages).
United States Patent Office Advisory Action for U.S. Appl. No. 11/856,740 dated Feb. 10, 2011 (3 pages).
United States Patent Office Action for U.S. Appl. No. 11/856,740 dated Dec. 6, 2010 (12 pages).
United States Patent Office Action for U.S. Appl. No. 11/856,740 dated Jun. 29, 2010 (10 pages).
United States Patent Office Action for U.S. Appl. No. 12/180,259 dated Jul. 5, 2011 (11 pages).
United States Patent Office Notice of Allowance for U.S. Appl. No. 12/180,259 dated Dec. 19, 2011 (6 pages).
United States Patent Office Notice of Allowance for U.S. Appl. No. 13/442,263 dated Dec. 19, 2012 (13 pages).
United States Patent Office Notice of Allowance for U.S. Appl. No. 13/442,263 dated Feb. 25, 2013 (8 pages).
United States Patent Office Notice of Allowance for U.S. Appl. No. 13/442,263 dated Jun. 12, 2013 (8 pages).
United States Patent Office Final Rejection for U.S. Appl. No. 13/442,263 dated Dec. 6, 2013 (8 pages).
United States Patent Office Notice of Allowance for U.S. Appl. No. 13/442,263 dated Apr. 15, 2014 (8 pages).
United States Patent Office Action for U.S. Appl. No. 14/273,895 dated Aug. 20, 2014 (8 pages).
United States Patent Office Action for U.S. Appl. No. 14/273,895 dated Dec. 24, 2014 (7 pages).
United States Patent Office Notice of Allowance for U.S. Appl. No. 14/273,895 dated Apr. 1, 2015 (8 pages).
United States Patent Office Action for U.S. Appl. No. 14/790,376 dated Jan. 22, 2016 (14 pages).
United States Patent Office Action for U.S. Appl. No. 13/318,457 dated Jun. 6, 2013 (12 pages).
United States Patent Office Final Rejection for U.S. Appl. No. 13/318,457 dated Nov. 27, 2013 (13 pages).
United States Patent Office Action for U.S. Appl. No. 12/694,965 dated May 17, 2012 (13 pages).
United States Patent Office Notice of Allowance for U.S. Appl. No. 12/694,965 dated Nov. 2, 2012 (8 pages).
United States Patent Office Notice of Allowance for U.S. Appl. No. 12/694,965 dated Nov. 19, 2012 (4 pages).
United States Patent Office Notice of Allowance for U.S. Appl. No. 13/768,594 dated Oct. 29, 2013 (7 pages).
United States Patent Office Action for U.S. Appl. No. 13/768,594 dated Jul. 10, 2013 (14 pages).
United States Patent Office Action for U.S. Appl. No. 14/138,592 dated Jul. 28, 2014 (17 pages).
United States Patent Office Action for U.S. Appl. No. 14/138,592 dated Dec. 9, 2014 (14 pages).
United States Patent Office Action for U.S. Appl. No. 11/856,740 dated Aug. 16, 2013 (14 pages).
United States Patent Office Notice of Allowance for U.S. Appl. No. 11/856,740 dated Apr. 1, 2014 (8 pages).
United States Patent Office Action for U.S. Appl. No. 14/461,597 dated Jan. 30, 2015 (19 pages).
United States Patent Office Action for U.S. Appl. No. 14/641,962 dated Sep. 22, 2015 (16 pages).
United States Patent Office Action for U.S. Appl. No. 14/754,787 dated Oct. 30, 2015 (20 pages).
United States Patent Office Action for U.S. Appl. No. 14/213,940 dated Oct. 29, 2015 (33 pages).
United States Patent Office Action for U.S. Appl. No. 14/213,961 dated Oct. 30, 2015 (37 pages).
Partial International Search for Application No. PCT/US2009/031117 dated Apr. 16, 2009 (4 pages).
International Search Report and Written Opinion for Application No. PCT/US2006/026976 dated Feb. 15, 2007 (14 pages).
International Search Report for Application No. PCT/US2006/026947 dated Nov. 17, 2006 (4 pages).
International Preliminary Examination Report for Application No. PCT/US2006/026947 dated Jan. 24, 2008 (10 pages).
International Search Report for Application No. PCT/US08/50374 dated Oct. 28, 2008 (7 pages).
International Preliminary Report on Patentability for Application No. PCT/US08/50374 dated Jul. 14, 2009 (12 pages).
International Search Report and Written Opinion for Application No. PCT/US2009/031117 dated Sep. 24, 2009 (13 pages).
Invitation to Pay Additional Fees and Partial International Search Report for International Application No. PCT/US2009/051569 dated Oct. 15, 2009 (4 pages).
International Search Report and Written Opinion for Application No. PCT/US2009/051569 dated May 20, 2010 (11 pages).
International Search Report and Written Opinion for Application No. PCT/US2010/33316 dated Jul. 14, 2010 (10 pages).
International Search Report and Written Opinion for Application No. PCT/US2010/33317 dated Aug. 17, 2010 (10 pages).

(56) References Cited

OTHER PUBLICATIONS

International Search Report and Written Opinion for Application No. PCT/US2010/022246 dated Nov. 10, 2010 (7 pages).
International Search Report and Written Opinion for Application No. PCT/US2007/078343 dated Apr. 3, 2008 (12 pages).
International Search Report and Written Opinion for Application No. PCT/US2014/029335, dated Jul. 2, 2014 (11 pages).
Chinese Patent Office Action for Application No. 2014800277613 dated Nov. 1, 2016 (18 pages including translation).
United States Patent Office Notice of Allowance for U.S. Appl. No. 14/790,376 dated Aug. 2, 2016 and Aug. 19, 2016 (10 pages).
United States Patent Office Action for U.S. Appl. No. 15/076,216 dated Sep. 1, 2016 (6 pages).
United States Patent Office Notice of Allowance for U.S. Appl. No. 14/213,961 dated Jun. 20, 2016 (8 pages).
Co-pending U.S. Appl. No. 15/076,216, filed Mar. 21, 2016, deLong et al.
Co-pending U.S. Appl. No. 15/142,448, filed Apr. 29, 2016, Bosanac et al.
Katritzky, A.R. et al., "Benzotriazole mediated amino-, amido-, alkoxy- and alkylthio-alkylation," Tetrahedron (2005) 61:2555-2581.
PubChem, AC1NQAJU (compound sumary for CID 5172372) '372' date created: Sep. 26, 2005 date access: Jan. 5, 2016, 10 pages.
International Search Report and Written Opinion for Application No. PCT/US2015/61177 dated Feb. 2, 2016 (16 pages).

COMBINATION THERAPY

CROSS-REFERENCE TO RELATED APPLICATIONS

This application is a continuation of U.S. patent application Ser. No. 14/213,940, filed Mar. 14, 2014, and claims priority to U.S. Provisional Application Ser. No. 61/787,883, filed Mar. 15, 2013, which are incorporated by reference herein in their entireties.

INTRODUCTION

A number of ocular conditions are caused by, or aggravated by, damage to the optic nerve head, degeneration of ocular tissues, and/or elevated intraocular pressure (IOP). For example, "glaucomas" are a group of debilitating eye diseases that are a leading cause of irreversible blindness in the United States and other developed nations. There is a continuing need for therapies that control elevated IOP to limit glaucomatous damage without undesirable side-effects.

SUMMARY

In one aspect, the disclosure may provide a composition comprising:

a) a compound according to formula (I):

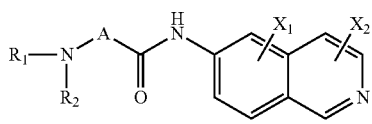
(I)

or a pharmaceutically acceptable salt thereof, wherein:

$R_1$ and $R_2$ are independently selected from the group consisting of hydrogen and $C_1$-$C_4$ alkyl, or $R_1$ and $R_2$ are taken together with the nitrogen atom to which they are attached to form a ring of 3, 4, 5, 6, 7 or 8 member atoms;

A is selected from the group consisting of —$CH_2NH$—, —$CH(R_{10})$—, —$C(CH_3)(R_{10})$—, —$CH_2CH_2$—, —$CH(R_{10})CH_2$—, —$CH_2CH_2CH(R_{10})$—, —$CH_2CH(R_{10})$—, and —$C(CH_3)(R_{10})CH_2$—;

each $R_{10}$ is independently selected from the group consisting of alkyl, alkenyl, alkynyl, amino, aryl, heteroaryl, cycloalkyl or heterocycloalkyl, any of which may be optionally substituted; and $X_1$ and $X_2$ are independently selected from the group consisting of hydrogen, hydroxy, halogen, alkyl, amino, nitro, cyano, carbonyl, carbonylamino, alkoxy, aryloxy, sulfonyl, sulfonamido, thioalkyl, and carboxyl; and b) a prostaglandin or a prostaglandin analog.

In another aspect, the disclosure may provide a compound according to formula (II):

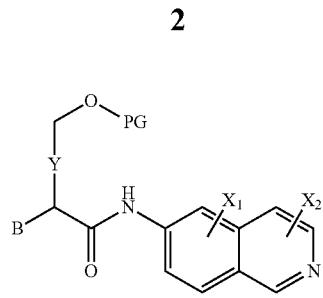
(II)

or a pharmaceutically acceptable salt thereof, wherein:

Y is selected from the group consisting of alkylene, aryl, heteroaryl, cycloalkyl, and heterocyclyl, any of which may be optionally substituted;

B is selected from the group consisting of —$NR_1R_2$, —$CH_2NR_1R_2$, —$CH(R_{10})R_2$, —$CCH_3(R_{10})$ $R_2$, —$NHCH(R_{10})R_2$, —$N(CH_3)R_2$, —$CH_2CH_2R_2$, —$CH(R_{10})CH_2R_2$, and —$CH_2CH(R_{10})R_2$;

$R_1$, $R_2$ and $R_{10}$ are each independently selected from the group consisting of hydrogen, alkyl, alkenyl, alkynyl, amino, aryl, heteroaryl, cycloalkyl and heterocycloalkyl, any of which may be optionally substituted;

$X_1$ and $X_2$ are independently selected from the group consisting of hydrogen, hydroxy, halogen, alkyl, amino, nitro, cyano, carbonyl, carbonylamino, alkoxy, aryloxy, sulfonyl, sulfonamido, thioalkyl, and carboxyl; and PG is the acyl radical of a prostaglandin or a prostaglandin analog.

In another aspect, the disclosure may provide a compound of formula (III):

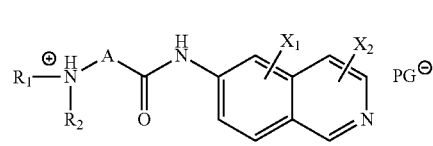
(III)

wherein:

$R_1$ and $R_2$ are independently selected from the group consisting of hydrogen and $C_1$-$C_4$ alkyl, or $R_1$ and $R_2$ are taken together with the nitrogen atom to which they are attached to form a ring of 3, 4, 5, 6, 7 or 8 member atoms;

A is selected from the group consisting of —$CH_2NH$—, —$CH(R_{10})$—, —$C(CH_3)(R_{10})$—, —$CH_2CH_2$—, —$CH(R_{10})CH_2$—, —$CH_2CH_2CH(R_{10})$—, —$CH_2CH(R_{10})$—, and —$C(CH_3)(R_{10})CH_2$—;

each $R_{10}$ is independently selected from the group consisting of alkyl, alkenyl, alkynyl, amino, aryl, heteroaryl, cycloalkyl or heterocycloalkyl, any of which may be optionally substituted;

$X_1$ and $X_2$ are independently selected from the group consisting of hydrogen, hydroxy, halogen, alkyl, amino, nitro, cyano, carbonyl, carbonylamino, alkoxy, aryloxy, sulfonyl, sulfonamido, thioalkyl, and carboxyl; and $PG_\ominus$ is a deprotonated free acid of a prostaglandin or a prostaglandin analog.

In another aspect, the disclosure may provide a composition comprising:

a) (rac)-2-(dimethylamino)-N-(1-hydroxyisoquinolin-6-yl)-2-(thiophen-3-yl)acetamide hydrochloride; and b) a prostaglandin selected from the group consisting of latanoprost, bimatoprost, travoprost, tafluprost, AR-102, cloprostenol, latanoprostene bunod, unoprostone, $PGF_{2\alpha}$ and fluprostenol.

In another aspect, the disclosure may provide a composition comprising:

a) (R)-2-(dimethylamino)-N-(1-hydroxyisoquinolin-6-yl)-2-(thiophen-3-yl)acetamide hydrochloride; and b) a prostaglandin selected from the group consisting of latanoprost, bimatoprost, travoprost, tafluprost, AR-102, cloprostenol, latanoprostene bunod, unoprostone, $PGF_{2\alpha}$ and fluprostenol.

In another aspect, the disclosure may provide a composition comprising:

a) (S)-2-(dimethylamino)-N-(1-hydroxyisoquinolin-6-yl)-2-(thiophen-3-yl)acetamide hydrochloride; and b) a prostaglandin selected from the group consisting of latanoprost, bimatoprost, travoprost, tafluprost, AR-102, cloprostenol, latanoprostene bunod, unoprostone, $PGF_{2\alpha}$ and fluprostenol.

In another aspect, the disclosure may provide a composition comprising:

a) (rac)-4-(3-amino-1-(isoquinolin-6-ylamino)-1-oxopropan-2-yl)benzyl 2,4-dimethylbenzoate dimesylate; and b) a prostaglandin selected from the group consisting of latanoprost, bimatoprost, travoprost, tafluprost, AR-102, cloprostenol, latanoprostene bunod, unoprostone, $PGF_{2\alpha}$ and fluprostenol.

In another aspect, the disclosure may provide a composition comprising:

a) (R)-4-(3-amino-1-(isoquinolin-6-ylamino)-1-oxopropan-2-yl)benzyl 2,4-dimethylbenzoate dimesylate; and b) a prostaglandin selected from the group consisting of latanoprost, bimatoprost, travoprost, tafluprost, AR-102, cloprostenol, latanoprostene bunod, unoprostone, $PGF_{2\alpha}$ and fluprostenol.

In another aspect, the disclosure may provide a composition comprising:

a) (S)-4-(3-amino-1-(isoquinolin-6-ylamino)-1-oxopropan-2-yl)benzyl 2,4-dimethylbenzoate dimesylate; and b) a prostaglandin selected from the group consisting of latanoprost, bimatoprost, travoprost, tafluprost, AR-102, cloprostenol, latanoprostene bunod, unoprostone, $PGF_{2\alpha}$ and fluprostenol.

In another aspect, the disclosure may provide a method of treating an ocular disorder in a subject in need of treatment, comprising administering to the subject a compound or composition described herein. In some embodiments, the ocular disorder is glaucoma.

In another aspect, the disclosure may provide a method of reducing intraocular pressure in a subject in need thereof, comprising topically administering to an eye of the subject a compound or composition described herein.

Other aspects and embodiments of the disclosure will become apparent in light of the following description.

DETAILED DESCRIPTION

Figure 1:
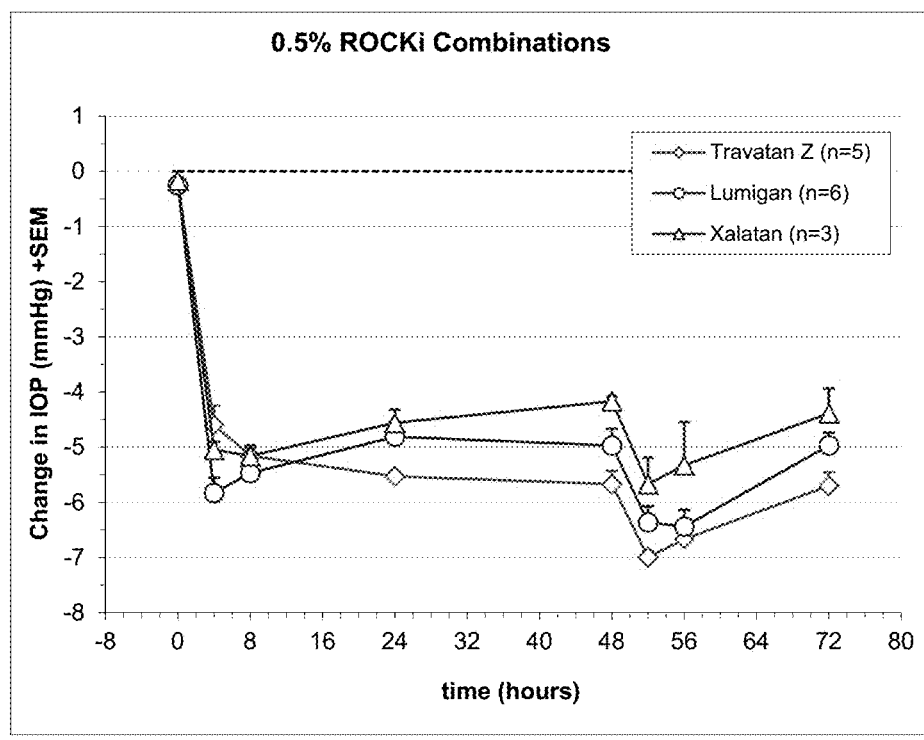
FIG. 1 is a graph showing intraocular pressure following administration of compositions described in Example 4.

Compositions that include an isoquinoline compound (e.g., a compound of formula (I)) and a prostaglandin or prostaglandin analog (e.g., latanoprost, bimatoprost, travoprost, tafluprost, AR-102, cloprostenol, latanoprostene bunod, unoprostone, $PGF_{2\alpha}$ or fluprostenol) are described herein. Also described herein are compounds of formula (II), which include an isoquinoline compound that is covalently linked to a prostaglandin or a prostaglandin analog, and compounds of formula (III), which are salts of an isoquinoline compound and a free acid of a prostaglandin or a prostaglandin analog. Such compounds and compositions may be effective for treating ocular disorders such as glaucoma, for example, by lowering intraocular pressure.

Before any embodiments of the disclosure are detailed, it is to be understood that the present disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Definitions

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

"Acyl" or "carbonyl" refers to the group —C(O)R wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, any of which may be optionally substituted, e.g., with one or more substituents. For example, when R is alkyl, such a group may be referred to as an alkylcarbonyl group.

"Administering" as used herein refers to administration of the compounds as needed to achieve a desired effect.

"Alkoxy" refers to the group —O—R wherein R is alkyl, alkenyl, alkynyl, cycloalkyl or heterocyclyl, any of which may be optionally substituted, e.g., with one or more substituents.

"Alkyl" refers to a saturated aliphatic hydrocarbon chain, which may be straight or branched. An alkyl group may have an indicated number of carbon atoms. For example, $C_1$-$C_{12}$ alkyl refers to an alkyl group having from 1 to 12 (inclusive) carbon atoms. $C_1$-$C_4$ alkyl refers to an alkyl group having 1, 2, 3 or 4 carbon atoms, such as methyl, ethyl, n-propyl, isopropyl, n-butyl, sec-butyl or tert-butyl. An alkyl group may be optionally substituted, e.g., with one or more substituents.

"Alkylene" refers to a divalent alkyl group, e.g., —CH$_2$—, —CH$_2$CH$_2$—, —CH$_2$CH$_2$CH$_2$— or —CH$_2$CH(CH$_3$)CH$_2$—. An alkyl or alkylene may be optionally substituted, e.g., with one or more substituents.

"Alkenyl" refers to a straight or branched hydrocarbon chain having one or more double bonds. An alkenyl group may have an indicated number of carbon atoms. For example, C$_2$-C$_{12}$ alkenyl refers to an alkenyl group having from 2 to 12 (inclusive) carbon atoms. C$_2$-C$_4$ alkenyl refers to an alkenyl group having 2, 3 or 4 carbon atoms. Examples of alkenyl groups include, but are not limited to, allyl, propenyl, 2-butenyl, 3-hexenyl and 3-octenyl groups. One of the double bond carbons may optionally be the point of attachment of the alkenyl substituent. The term "alkenylene" refers to a divalent alkenyl, e.g., —CH═CH—, —CH═CH$_2$CH$_2$— or —CH═C═CH—. An alkenyl or alkenylene may be optionally substituted, e.g., with one or more substituents.

The term "alkynyl" refers to a straight or branched hydrocarbon chain having one or more triple bonds. An alkynyl group may have an indicated number of carbon atoms. For example, C$_2$-C$_{12}$ alkynyl refers to an alkynyl group having from 2 to 12 (inclusive) carbon atoms. C$_2$-C$_4$ alkynyl refers to an alkynyl group having 2, 3 or 4 carbon atoms. Examples of alkynyl groups include, but are not limited to, ethynyl, propargyl, and 3-hexynyl. One of the triple bond carbons may optionally be the point of attachment of the alkynyl substituent. The term "alkynylene" refers to a divalent alkynyl, e.g., —C≡C— or —C≡C—CH$_2$—. An alkynyl or alkynylene may be optionally substituted, e.g., with one or more substituents.

"Amino" refers to the group —NR'R" wherein R' and R" are each independently selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, or R' and R", together with the nitrogen to which they are attached, may form a ring. Examples of amino groups include, but are not limited to, —NH$_2$, alkylamino groups such as —NHCH$_3$, —NHCH$_2$CH$_3$ and —NHCH(CH$_3$)$_2$, dialkylamino groups such as —N(CH$_3$)$_2$ and —N(CH$_2$CH$_3$)$_2$, and arylamino groups such as —NHPh. Examples of cyclic amino groups include, but are not limited to, aziridinyl, azetidinyl, pyrrolidinyl, piperidino, piperazinyl, perhydrodiazepinyl, morpholino, and thiomorpholino. The groups R' and R" may be optionally substituted, e.g., with one or more substituents, or when R' and R" together with the nitrogen to which they are attached form a ring, the ring may be optionally substituted, e.g., with one or more substituents.

"AR-102" refers to the compound 3-hydroxy-2,2-bis(hydroxymethyl)propyl7-((1R,2R,3R,5S)-2-((R)-3-(benzo[b]thiophen-2-yl)-3-hydroxypropyl)-3,5-dihydroxycyclopentyl)heptanoate. "AR-102 free acid" refers to the compound 7-((1R,2R,3R,5S)-2-((R)-3-(benzo[b]thiophen-2-yl)-3-hydroxypropyl)-3,5-dihydroxycyclopentyl)heptanoic acid.

"Aryl" refers to an aromatic monocyclic, bicyclic, or tricyclic hydrocarbon ring system, wherein any ring atom capable of substitution can be substituted (e.g., with one or more substituents). The substituents may be positioned at various locations on an aryl group. For example, substituents on a phenyl group may be located at an ortho-position, a meta-position, the para-position, or combinations thereof. Examples of aryl groups include, but are not limited to, phenyl, naphthyl, and anthracenyl.

"Arylalkyl" refers to an alkyl group in which an alkyl hydrogen atom is replaced with an aryl group. Arylalkyl includes groups in which more than one hydrogen atom has been replaced with an aryl group. Examples of arylalkyl groups include but are not limited to benzyl, 2-phenylethyl, 3-phenylpropyl, 9-fluorenyl, benzhydryl, and trityl groups. Arylalkyl groups can be optionally substituted, e.g., with one or more substituents on either the alkyl portion or the aryl portion of the arylalkyl group.

"Aryloxy" refers to the group —O—R wherein R is aryl or heteroaryl, either of which may be optionally substituted, e.g., with one or more substituents.

"Buffer" or "buffer system" refers to a compound or combination of compounds that provide a buffering system in solution that exhibits buffering capacity, that is, the capacity to neutralize, within limits, either acids or bases with relatively little or no change in the original pH. The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components.

"Carboxyl" refers to the group —C(═O)OR, wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl any of which may be optionally substituted, e.g., with one or more substituents.

"Carbonylamino" or "amido" refers to the group —C(O)NR'R" wherein R' and R" are independently selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, or R' and R", together with the nitrogen to which they are attached, may form a ring. The groups R' and R" may be optionally substituted, e.g., with one or more substituents, or when R' and R" together with the nitrogen to which they are attached form a ring, the ring may be optionally substituted, e.g., with one or more substituents.

"Cycloalkyl" refers to nonaromatic, saturated or partially unsaturated monocyclic, bicyclic, tricyclic or polycyclic hydrocarbon groups. Cycloalkyl groups may include about 3 to about 12 carbon atoms. For example, monocyclic cycloalkyl groups may include 3 to 10 carbon atoms, e.g., 3, 4, 5, 6, 7 or 8 carbon atoms. Bicyclic carbocyclic groups contain 8 to 12 carbon atoms, e.g., 9 or 10 carbon atoms. Any ring atom can be substituted (e.g., with one or more substituents). Cycloalkyl groups include fused, spiro, and bridged bicyclic ring systems. Examples of cycloalkyl groups include, but are not limited to, cyclopropyl, cyclobutyl, cyclopentyl, cyclohexyl, cyclohexenyl, cyclohexadienyl, methylcyclohexyl, adamantyl, norbornyl and norbornenyl.

"Cycloalkylalkyl", as used herein, refers to an alkyl group substituted with a cycloalkyl group.

"Excipient" refers to physiologically compatible additives useful in preparation of a pharmaceutical composition. Examples of pharmaceutically acceptable carriers and excipients can, for example, be found in Remington Pharmaceutical Science, 16$^{th}$ Ed.

"Haloalkyl" as used herein refers to an alkyl group in which one or more hydrogen atoms are replaced with a halogen, and includes alkyl moieties in which all hydrogens have been replaced with halogens (e.g., perfluoroalkyl such as CF$_3$).

"Halogen" or "halo" refers to fluoro, chloro, bromo or iodo moieties.

"Heteroalkyl" refers to an alkyl group, as defined herein, wherein at least one carbon atom of the alkyl group is replaced with a heteroatom. Suitable heteroalkyl groups include, but are not limited to, methoxymethyl (—CH$_2$—O—CH$_3$).

"Heteroaryl" or "heteroaromatic" refers to an aromatic monocyclic, bicyclic or tricyclic ring having one or more heteroatoms. For example a heteroaryl group may be an aromatic 5-8 membered monocyclic ring having 1-4 heteroatoms, an 8-12 membered bicyclic ring having 1-6 heteroatoms, or an 11-14 membered tricyclic ring system having 1-9 heteroatoms. Heteroaryl groups can contain fused rings, which are rings that share one or more common atoms. Any ring atom capable of substitution can be substituted (e.g., with one or more substituents). Examples of heteroaryl groups include, but are not limited to, tetrazoylyl, triazolyl, thienyl, thiazolyl, isothiazolyl, purinyl, pyrimidyl, pyridyl, pyrazinyl, pyridazinyl, pyrrolyl, imidazolyl, pyrazolyl, oxazolyl, isoxazolyl, furanyl, quinolinyl, isoquinolinyl, quinoxalinyl, quinazolinyl, cinnolinyl, indolyl, isoindolyl, indolizinyl, indazolyl, benzimidazolyl, phthalazinyl, pteridinyl, carbazolyl, carbolinyl, phenanthridinyl, acridinyl, phenanthrolinyl, phenazinyl and naphthyridinyl.

The term "heteroarylalkyl", as used herein, refers to an alkyl group substituted with a heteroaryl group.

"Heteroatom" refers to an atom other than carbon in the ring of a heterocyclic group or a heteroaromatic group or the chain of a heteroalkyl group. For example, heteroatoms may be selected from the group consisting of nitrogen, oxygen, silicon, phosphorus and sulfur. Particularly suitable heteroatoms are nitrogen, oxygen and sulfur. Groups containing more than one heteroatom may contain different heteroatoms.

"Heterocyclyl" or "heterocycloalkyl" refers to a nonaromatic, saturated or partially unsaturated hydrocarbon ring system containing at least one heteroatom. Heterocyclyl groups may include about 3 to about 12 member atoms. For example, monocyclic cycloalkyl groups may include 3 to 10 member atoms, e.g., 3, 4, 5, 6, 7 or 8 member atoms. Bicyclic carbocyclic groups contain 8 to 12 member atoms, e.g., 9 or 10 member atoms. Any ring atom capable of substitution can be substituted (e.g., with one or more substituents). Heterocyclyl groups include fused, spiro, and bridged bicyclic ring systems. Examples of heterocyclyl groups include, but are not limited to, epoxy, tetrahydrofuranyl, homopiperidinyl, tetrahydrothienyl, tetrahydropyranyl, piperidinyl, piperazinyl, morpholinyl, pyrrolinyl, pyrimidinyl, pyrrolidinyl, indolinyl, tetrahydropyridinyl, dihydropyran, thianthrene, pyran, benzopyran, xanthene, phenoxathiin, phenothiazinyl, furazanyl, lactones, lactams such as azetidinones and pyrrolidinones, sultams, sultones, and the like.

The term "heterocyclylalkyl" or "heterocycloalkylalkyl", as used herein, refers to an alkyl group substituted with a heterocyclyl group.

"Hydroxy" or "hydroxyl" refers to the group —OH.

"Linker" means a chain of n member atoms where n is an integer from 1 to 4.

"Member atom" means a carbon, nitrogen, oxygen or sulfur atom. Member atoms may be substituted up to their normal valence.

The term "mercapto" or "thiol" refers to an —SH radical. The term "thioalkoxy" or "thioether" refers to an —S-alkyl radical. The term "thioaryloxy" refers to an —S-aryl radical.

The term "ocular disorder" as used herein includes, but is not limited to, glaucoma, allergy, cancers of the eye, neurodegenerative diseases of the eye, dry eye, and corneal epithelial damage. A "method of treating an ocular disorder" may refer to a method of treating glaucoma, allergy, cancers of the eye, neurodegenerative diseases of the eye, dry eye, and corneal epithelial damage, or may refer to a method of preserving retinal ganglion cells.

The term "oxo" refers to an oxygen atom, which forms a carbonyl when attached to carbon, an N-oxide when attached to nitrogen, and a sulfoxide or sulfone when attached to sulfur. The term "thioxo" refers to a sulfur atom, which forms a thiocarbonyl when attached to carbon.

"Phosphonate" refers to —P(O)(OR)$_2$, wherein each R is independently selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, each of which may be optionally substituted, e.g., with one or more substituents.

A "prostaglandin" refers to any compound having a prostanoic acid skeleton:

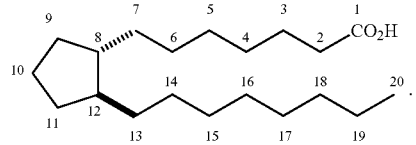

A "prostaglandin analog" refers to a compound that has the potential to bind to a prostaglandin receptor. Prostaglandin analogs include protected prostaglandins or prostaglandin prodrugs, e.g. prostaglandins with esters or amides at the C1, C9, C11 and/or C15 positions.

"Prostaglandin free acid" refers to a prostaglandin or prostaglandin analog that has a carboxylic acid moiety at the C1 position.

"Prostaglandin F analog," "PGF analog" or "analog of PGF$_{2\alpha}$" refers to a compound, generally structurally similar to naturally occurring PGF$_{2\alpha}$, which has the potential to bind to and activate a prostaglandin F-type receptor. F-type receptors include, but are not limited to the FP receptor.

"Prostaglandin E analog," "PGE analog," "analog of PGE$_2$" or "analog of PGE$_1$" refers to a compound, generally structurally similar to naturally occurring PGE$_2$ or PGE$_1$, which has the potential to bind to and activate a prostaglandin E-type receptor. E-type receptors include, but are not limited to the EP1, EP2, EP3 and EP4 receptors.

"Prostaglandin D analog," "PGD analog" or "analog of PGD$_2$" refers to a compound, generally structurally similar to naturally occurring PGD$_2$, which has the potential to bind to and activate a prostaglandin D-type receptor. D-type receptors include, but are not limited to the DP1 and DP2 receptors.

"Ring" means a collection of member atoms that are cyclic. Rings may be carbocyclic, aromatic, or heterocyclic or heteroaromatic, and may be substituted or unsubstituted, and may be saturated or unsaturated. Ring junctions with the main chain may be fused or spirocyclic. Rings may be monocyclic or bicyclic. Rings contain at least 3 member atoms and at most 12 member atoms. Monocyclic rings may contain 3 to 10 member atoms and bicyclic rings may contain from 8 to 12 member atoms. Bicyclic rings themselves may be fused or spirocyclic. Rings may be optionally substituted or unsubstituted, e.g., with one or more substituents.

"ROCKi" as used herein refers to an inhibitor of a Rho-associated protein kinase (ROCK).

"Substituent" refers to a group "substituted" on a group such as an alkyl, alkylene, alkenyl, alkynyl, cycloalkyl, cycloalkylalkyl, heterocyclyl, heterocyclylalkyl, aryl, arylalkyl, heteroaryl or heteroarylalkyl group, at any substitutable atom of that group. Suitable substituents include, without limitation: acyl, alkoxy, alkyl, alkenyl, alkynyl, amino, aryl, arylalkyl, carbonylamino, carboxy, cycloalkyl, cycloalkylalkyl, cyano, halo, haloalkyl, heteroalkyl, heteroaryl, heteroarylalkyl, heterocyclyl, heterocyclylalkyl, hydroxy, nitro, oxo (e.g., C═O), phosphonate, sulfinyl, sulfonyl, sulfonate, sulfonamido, thioamido, thiol, thioalkyl, thioxo (e.g., C═S), and ureido. In embodiments, substituents on a group are independently any one single, or any combination of the aforementioned substituents. In embodiments, a substituent may itself be substituted with any one of the above substituents.

The above substituents may be abbreviated herein, for example, the abbreviations Me, Et, Ph, Bn and Ac represent methyl, ethyl, phenyl, benzyl and acetyl respectively. A more comprehensive list of the abbreviations used by organic chemists of ordinary skill in the art appears in the first issue of each volume of the Journal of Organic Chemistry; this list is typically presented in a table entitled Standard List of Abbreviations. The abbreviations contained in said list, and all abbreviations used by organic chemists of ordinary skill in the art, are hereby incorporated by reference.

"Sulfinyl" refers to a —S(═O)R group, wherein R is selected from the group consisting of alkyl, alkenyl, alkynyl, aryl, cycloalkyl, heterocyclyl, heteroaryl, arylalkyl, cycloalkylalkyl, heteroarylalkyl and heterocyclylalkyl, any of which may be optionally substituted (e.g., with one or more substituents).

"Sulfonic acid" and "sulfonate" refer to —S(O)$_2$OH and —S(O)$_2$O$^-$ groups respectively "Sulfonyl" refers to a —S(O)$_2$R group, wherein R is selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, any of which may be optionally substituted (e.g., with one or more substituents).

"Sulfonamido" refers to a —S(O)$_2$NR'R" group wherein R' and R" are independently selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, any of which may be optionally substituted (e.g., with one or more substituents).

"Therapeutically effective amount" refers to a dosage of the compounds or compositions effective for influencing, reducing or inhibiting the activity of or preventing activation of a kinase. This term as used herein may also refer to an amount effective at bringing about a desired in vivo effect in an animal, preferably, a human, such as reduction in intraocular pressure.

"Thioalkyl" refers to the group —S-alkyl.

"Thioamido" refers to —C(S)NR'R" wherein R' and R" are independently selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, or R' and R", together with the nitrogen to which they are attached, may form a ring. The groups R' and R" may be optionally substituted, e.g., with one or more substituents, or when R' and R" together with the nitrogen to which they are attached form a ring, the ring may be optionally substituted, e.g., with one or more substituents.

"Treat" or "treating" as used herein refers to administering a regimen to the subject, e.g., the administration a compound or composition described herein, such that the disorder or at least one symptom of the disorder is healed, alleviated, relieved, altered, remedied, ameliorated, and/or improved. Treating includes administering an amount effective to alleviate, relieve, alter, remedy, ameliorate, improve and/or affect the disorder or the symptoms of the disorder. The treatment may inhibit deterioration or worsening of a symptom of a disorder.

"Ureido" refers to —N(R)C(O)NR'R", wherein each R, R' and R" is independently selected from the group consisting selected from the group consisting of hydrogen, alkyl, alkenyl, alkynyl, aryl, cycloalkyl, heterocyclyl, heteroaryl, arylalkyl, cycloalkylalkyl, heteroarylalkyl and heterocyclylalkyl, any of which may be optionally substituted (e.g., with one or more substituents).

Where substituent groups are specified by their conventional chemical formulae, written from left to right, they optionally encompass substituents resulting from writing the structure from right to left, e.g., —CH$_2$NH— optionally also recites —NHCH$_2$—. While certain lists of substituent groups include a group shown in both orientations, it should be expressly understood that any substituent group written in a certain direction (e.g., left to right) also encompasses the same group in the other direction (e.g., right to left).

In accordance with a convention used in the art, the group:

is used in structural formulas herein to depict a bond that is the point of attachment of the moiety or substituent to the core or backbone structure.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

It specifically is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

All percentages, ratios, and proportions used herein are percent by weight per volume (% wt/vol or w/v) unless otherwise specified.

Compounds

Compounds that may be used in compositions described herein include isoquinoline compounds. Such compounds and the compositions including them may have kinase inhibitory activity and thus may be useful in influencing or inhibiting the action of kinases, and in treatment and/or prevention of diseases or conditions influenced by kinases. Exemplary kinases that may be influenced include, but are not limited to, ROCK-I, ROCK-II, PKA, PKC, CAM Kinases, GRK-2, GRK-3, GRK-5 or GRK-6. For example, the kinase inhibited may be a Rho-associated protein kinase (ROCK).

Isoquinoline compounds that may be used in compositions and methods described herein include compounds of formula (I):

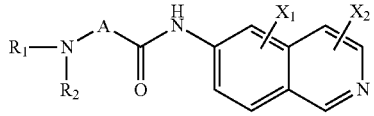

(I)

or a pharmaceutically acceptable salt thereof, wherein:

$R_1$ and $R_2$ are independently selected from the group consisting of hydrogen and $C_1$-$C_4$ alkyl, or $R_1$ and $R_2$ are taken together with the nitrogen atom to which they are attached to form a ring of 3, 4, 5, 6, 7 or 8 member atoms;

A is selected from the group consisting of —$CH_2NH$—, —$CH(R_{10})$—, —$C(CH_3)(R_{10})$—, —$CH_2CH_2$—, —$CH(R_{10})CH_2$—, —$CH_2CH_2CH(R_{10})$—, —$CH_2CH(R_{10})$—, and —$C(CH_3)(R_{10})CH_2$—;

each $R_{10}$ is independently selected from the group consisting of alkyl, alkenyl, alkynyl, amino, aryl, heteroaryl, cycloalkyl or heterocycloalkyl, any of which may be optionally substituted; and $X_1$ and $X_2$ are independently selected from the group consisting of hydrogen, hydroxy, halogen, alkyl, amino, nitro, cyano, carbonyl, carbonylamino, alkoxy, aryloxy, sulfonyl, sulfonamido, thioalkyl, and carboxyl.

In some embodiments of formula (I), $X_1$ is hydrogen, $X_2$ is hydroxy, $R_1$ is alkyl (e.g., methyl), $R_2$ is alkyl (e.g., methyl), A is —$CH(R_{10})$—, and $R_{10}$ is aryl (e.g., phenyl).

In some embodiments of formula (I), $X_1$ is hydrogen, $X_2$ is hydroxy, $R_1$ and $R_2$ together form a heterocyclyl ring, A is —$CH(R_{10})$—, and $R_{10}$ is alkyl.

In some embodiments of formula (I), $X_1$ and $X_2$ are hydrogen, $R_1$ is alkyl (e.g., methyl), and $R_2$ is alkyl (e.g., methyl), A is —$CH(R_{10})$—, and $R_{10}$ is heteroaryl (e.g., thienyl).

In some embodiments of formula (I), $X_1$ and $X_2$ are hydrogen, $R_1$ is hydrogen, and $R_2$ is hydrogen, A is —$CH_2CH(R_{10})$—, and $R_{10}$ is a substituted aryl group.

In some embodiments of formula (I), $X_1$ is hydrogen, $X_2$ is hydroxy, $R_1$ is alkyl (e.g., methyl), $R_2$ is alkyl (e.g., methyl), A is —$CH(R_{10})$—, and $R_{10}$ is heteroaryl (e.g., thienyl).

In some embodiments of formula (I), $X_1$ and $X_2$ are hydrogen, $R_1$ is alkyl (e.g., methyl), and $R_2$ is hydrogen, A is —$CH(R_{10})$—, and $R_{10}$ is heteroaryl (e.g., thienyl).

Isoquinoline compounds that may be used in compositions and methods described herein include compounds of formula (Ia) which is the same as its tautomeric form, also shown here for clarification purposes:

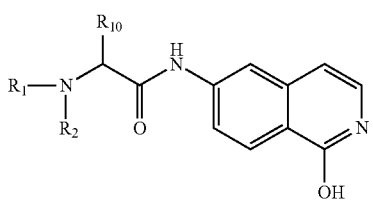

(Ia)

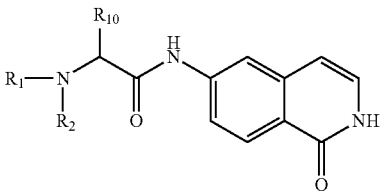

(Ia tautomer)

or a pharmaceutically acceptable salt thereof, wherein:

$R_1$ and $R_2$ are independently selected from the group consisting of hydrogen and $C_1$-$C_4$ alkyl, or $R_1$ and $R_2$ are taken together with the nitrogen atom to which they are attached to form a ring of 3, 4, 5, 6, 7 or 8 member atoms; and $R_{10}$ is selected from the group consisting of alkyl, alkenyl, alkynyl, amino, aryl, heteroaryl, cycloalkyl and heterocyclyl, any of which may be optionally substituted.

In some embodiments, $R_{10}$ is aryl (e.g., phenyl). In some embodiments, $R_{10}$ is heteroaryl (e.g., thienyl). In some embodiments, $R_1$ and $R_2$ are independently selected from the group consisting of hydrogen and methyl, or $R_1$ and $R_2$ are taken together with the nitrogen to which they are attached to form a heterocyclyl ring (e.g., pyrrolidone or piperidine).

Isoquinoline compounds that may be used in compositions and methods described herein include compounds of formula (Ib):

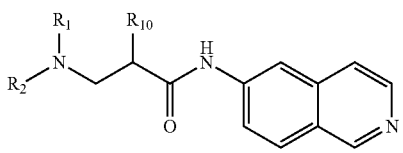

(Ib)

or a pharmaceutically acceptable salt thereof, wherein:

$R_1$ and $R_2$ are independently selected from the group consisting of hydrogen and $C_1$-$C_4$ alkyl, or $R_1$ and $R_2$ are taken together with the nitrogen atom to which they are attached to form a ring of 3, 4, 5, 6, 7 or 8 member atoms; and $R_{10}$ is selected from the group consisting of alkyl, alkenyl, alkynyl, amino, aryl, heteroaryl, cycloalkyl and heterocyclyl, any of which may be optionally substituted.

In some embodiments, $R_{10}$ is aryl (e.g., phenyl). In some embodiments, $R_{10}$ is aryl (e.g., phenyl) substituted with —$CH_2$—$OC(O)$—$R^a$, wherein $R^a$ is optionally substituted aryl (e.g., phenyl, e.g., 2,4-dimethylphenyl). In some embodiments, $R_1$ and $R_2$ are independently selected from the group consisting of hydrogen and methyl, or $R_1$ and $R_2$ are taken together with the nitrogen to which they are attached to form a heterocyclyl ring (e.g., pyrrolidone or piperidine).

In embodiments, the compound of formula (I) may be selected from the group consisting of:
(rac)-2-(dimethylamino)-N-(1-hydroxyisoquinolin-6-yl)-2-(thiophen-3-yl)acetamide;
(R)-2-(dimethylamino)-N-(1-hydroxyisoquinolin-6-yl)-2-(thiophen-3-yl)acetamide;
(S)-2-(dimethylamino)-N-(1-hydroxyisoquinolin-6-yl)-2-(thiophen-3-yl)acetamide;
(rac)-4-(3-amino-1-(isoquinolin-6-ylamino)-1-oxopropan-2-yl)benzyl 2,4-dimethylbenzoate;

(R)-4-(3-amino-1-(isoquinolin-6-ylamino)-1-oxopropan-2-yl)benzyl 2,4-dimethylbenzoate; and
(S)-4-(3-amino-1-(isoquinolin-6-ylamino)-1-oxopropan-2-yl)benzyl 2,4-dimethylbenzoate,
or a pharmaceutically acceptable salt thereof.

Compounds of formula (I) may be synthesized by methods known in the art. For example, compounds may be synthesized using methods described in U.S. Patent Publication No. 2009/0186917, which is hereby incorporated by reference in its entirety.

Also disclosed herein are compounds in which an isoquinoline compound is covalently linked to a prostaglandin or a prostaglandin analog. Such compounds include compounds of formula (II):

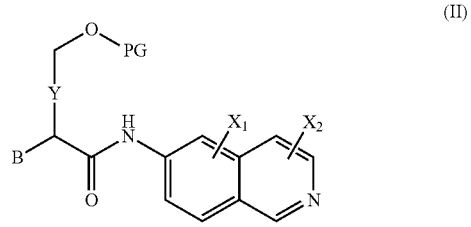

(II)

or a pharmaceutically acceptable salt thereof, wherein:

Y is selected from the group consisting of alkylene, aryl, heteroaryl, cycloalkyl, and heterocyclyl, any of which may be optionally substituted;

B is selected from the group consisting of —$NR_1R_2$, —$CH_2NR_1R_2$, —$CH(R_{10})R_2$, —$CCH_3(R_{10})$ $R_2$, —NHCH$(R_{10})R_2$, —$N(CH_3)R_2$, —$CH_2CH_2R_2$, —$CH(R_{10})CH_2R_2$, and —$CH_2CH(R_{10})R_2$;

$R_1$, $R_2$ and $R_{10}$ are each independently selected from the group consisting of hydrogen, alkyl, alkenyl, alkynyl, amino, aryl, heteroaryl, cycloalkyl and heterocycloalkyl, any of which may be optionally substituted;

$X_1$ and $X_2$ are independently selected from the group consisting of hydrogen, hydroxy, halogen, alkyl, amino, nitro, cyano, carbonyl, carbonylamino, alkoxy, aryloxy, sulfonyl, sulfonamido, thioalkyl, and carboxyl; and PG is the acyl radical of a prostaglandin or a prostaglandin analog.

An "acyl radical of a prostaglandin or a prostaglandin analog" refers to a prostaglandin or a prostaglandin analog in which the C1 position has the group —C(O)—. For example, acyl radicals of latanoprost, bimatoprost and travoprost are illustrated below:

Acyl radical of bimatoprost:

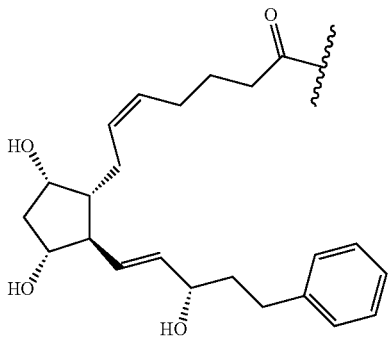

Acyl radical of travoprost:

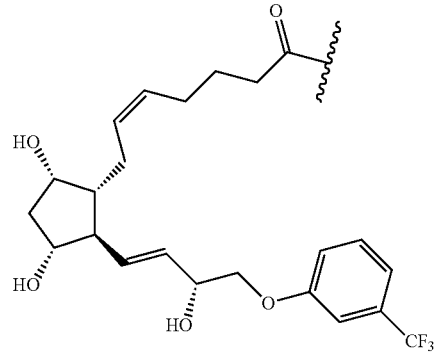

Acyl radical of latanoprost:

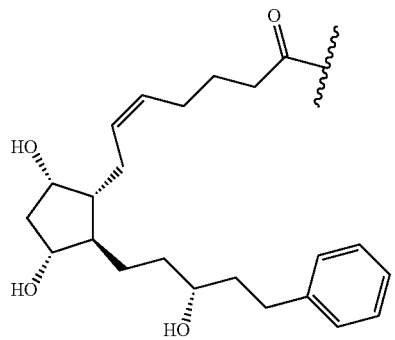

In some embodiments of formula (II), $X_1$ and $X_2$ are hydrogen, B is —$CH_2NR_1R_2$, $R_1$ is alkyl (e.g., methyl), $R_2$ is alkyl (e.g., methyl), and PG is the acyl radical of latanoprost.

In some embodiments of formula (II), $X_1$ and $X_2$ are hydrogen, B is —$CH_2NR_1R_2$, $R_1$ and $R_2$ are hydrogen, and PG is the acyl radical of latanoprost.

In some embodiments of formula (II), $X_1$ is hydrogen, $X_2$ is hydroxy, B is —$CH_2NR_1R_2$, $R_1$ and $R_2$ are hydrogen, and PG is the acyl radical of latanoprost.

In some embodiments of formula (II), $X_1$ is hydrogen, $X_2$ is hydroxy, B is —$NR_1R_2$, $R_1$ is hydrogen, $R_2$ is hydrogen, and PG is the acyl radical of travoprost.

In some embodiments of formula (II), $X_1$ is hydrogen, $X_2$ is hydroxy, B is —$NR_1R_2$, $R_1$ is alkyl (e.g., methyl), $R_2$ is alkyl (e.g., methyl), and PG is the acyl radical of latanoprost.

In some embodiments of formula (II), $X_1$ and $X_2$ are hydrogen, B is —$CH_2NR_1R_2$, $R_1$ is hydrogen, $R_2$ is hydrogen, and PG is the acyl radical of travoprost.

In some embodiments of formula (II), $X_1$ and $X_2$ are hydrogen, B is —$CH_2NR_1R_2$, $R_1$ is hydrogen, $R_2$ is hydrogen, and PG is the acyl radical of bimatoprost.

In some embodiments of formula (II), PG is the acyl radical of latanoprost, bimatoprost, travoprost, tafluprost, AR-102, cloprostenol, latanoprostene bunod, unoprostone, $PGF_{2\alpha}$ or fluprostenol.

Compounds of formula (II) may be synthesized according a method similar to that shown below in Scheme 1, wherein each R is independently a protecting group. One skilled in the art will appreciate that the starting protected prostaglandin free acid and isoquinoline can be prepared using known methods; see, for example, *Protective Groups in Organic Synthesis* (T. Green and P. Wuts; 3rd Edition; John Wiley and Sons, 1999). Step (a) may be conducted in a suitable solvent and in the presence of a suitable coupling agent, such as a carbodiimide. Following coupling in step (a), the product may be deprotected in step (b) using methods particular to the protecting groups that were used. It will be noted that while Scheme 1 illustrates coupling of latanoprost free acid and a specific isoquinoline compound, one skilled in the art will appreciate that such a general synthesis scheme could be applied to any prostaglandin free acid and isoquinoline compound bearing a suitably reactive functional group such as a hydroxy group, amine group, or the like. Specific syntheses including protecting and deprotecting steps are illustrated in the Examples.

Also disclosed herein are compounds in which an isoquinoline compound and a prostaglandin or a prostaglandin analog together form a salt. Such compounds include compounds of formula (III):

The compounds that may be used in compositions and methods described herein also include salts of isoquinoline compounds and prostaglandin free acids. Such compounds include compounds of formula (III):

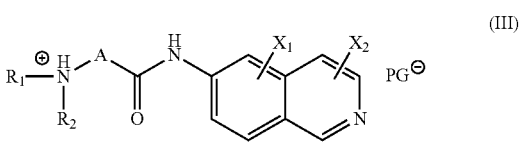

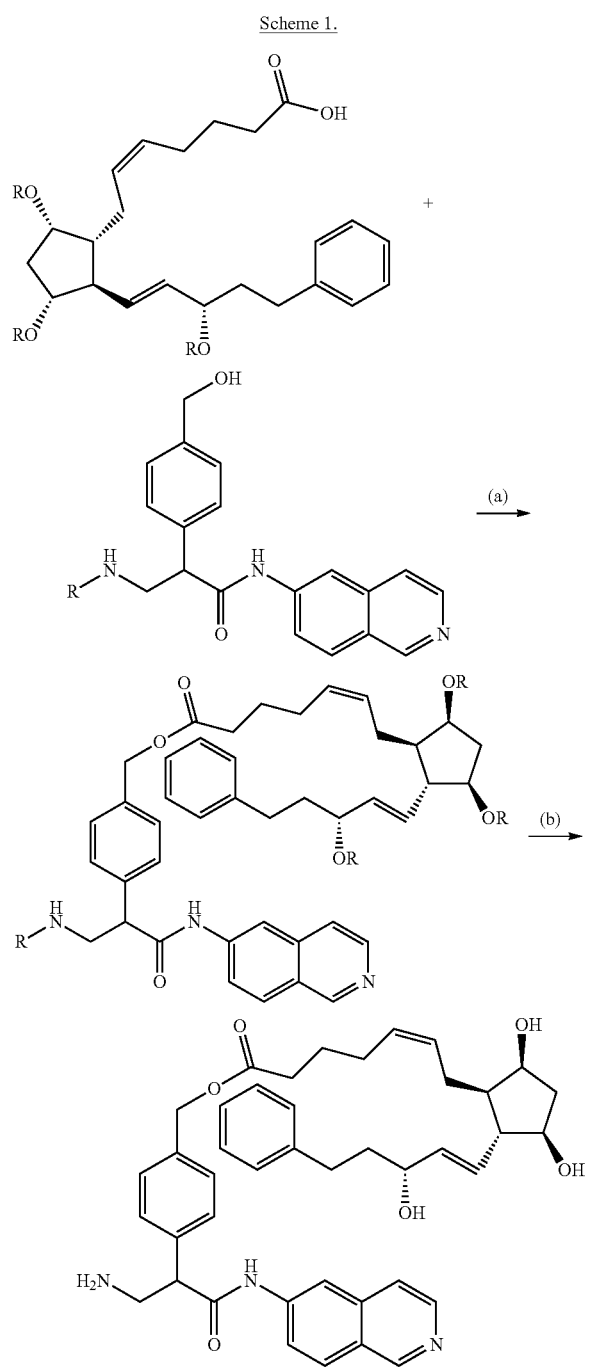

Scheme 1.

wherein:

$R_1$ and $R_2$ are independently selected from the group consisting of hydrogen and $C_1$-$C_4$ alkyl, or $R_1$ and $R_2$ are taken together with the nitrogen atom to which they are attached to form a ring of 3, 4, 5, 6, 7 or 8 member atoms;

A is selected from the group consisting of —$CH_2NH$—, —$CH(R_{10})$—, —$C(CH_3)(R_{10})$—, —$CH_2CH_2$—, —$CH(R_{10})CH_2$—, —$CH_2CH_2CH(R_{10})$—, —$CH_2CH(R_{10})$—, and —$C(CH_3)(R_{10})CH_2$—;

each $R_{10}$ is independently selected from the group consisting of alkyl, alkenyl, alkynyl, amino, aryl, heteroaryl, cycloalkyl or heterocycloalkyl, any of which may be optionally substituted;

$X_1$ and $X_2$ are independently selected from the group consisting of hydrogen, hydroxy, halogen, alkyl, amino, nitro, cyano, carbonyl, carbonylamino, alkoxy, aryloxy, sulfonyl, sulfonamido, thioalkyl, and carboxyl; and $PG_\ominus$ is a deprotonated free acid of a prostaglandin or a prostaglandin analog.

A "deprotonated free acid of a prostaglandin or a prostaglandin analog" refers to a prostaglandin or a prostaglandin analog in which the C1 position has the group —$C(O)O^-$. For example, deprotonated free acids of latanoprost, bimatoprost and travoprost are illustrated below:

Deprotonated bimatoprost free acid:

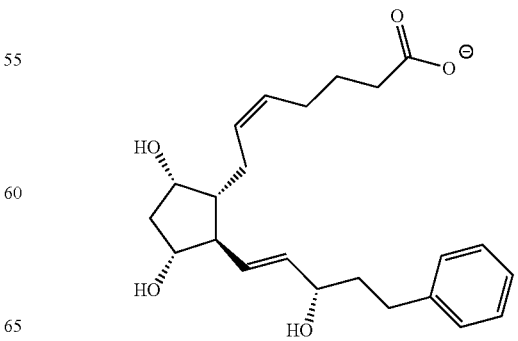

-continued

Deprotonated travoprost free acid:

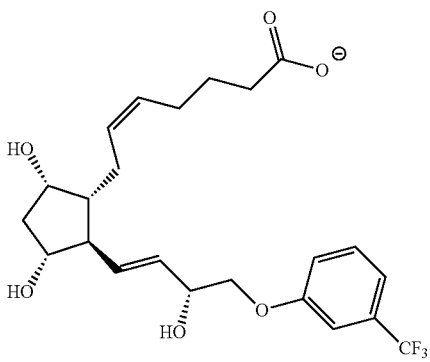

Deprotonated latanoprost free acid:

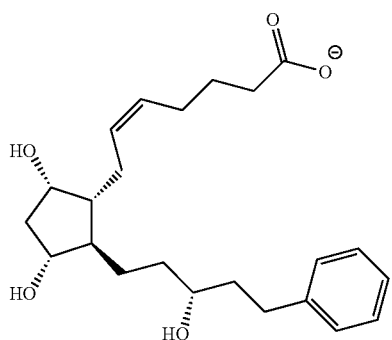

In some embodiments of formula (III), $X_1$ is hydrogen, $X_2$ is hydroxy, $R_1$ is alkyl (e.g., methyl), $R_2$ is alkyl (e.g., methyl), A is —CH($R_{10}$)—, and $R_{10}$ is aryl (e.g., phenyl).

In some embodiments of formula (III), $X_1$ is hydrogen, $X_2$ is hydroxy, $R_1$ and $R_2$ together form a heterocyclyl ring, A is —CH($R_{10}$)—, and $R_{10}$ is alkyl.

In some embodiments of formula (III), $X_1$ and $X_2$ are hydrogen, $R_1$ is alkyl (e.g., methyl), and $R_2$ is alkyl (e.g., methyl), A is —CH($R_{10}$)—, and $R_{10}$ is heteroaryl (e.g., thienyl).

In some embodiments of formula (III), $X_1$ and $X_2$ are hydrogen, $R_1$ is hydrogen, and $R_2$ is hydrogen, A is —CH$_2$CH($R_{10}$)—, and $R_{10}$ is a substituted aryl group.

In some embodiments of formula (III), $X_1$ is hydrogen, $X_2$ is hydroxy, $R_1$ is alkyl (e.g., methyl), $R_2$ is alkyl (e.g., methyl), A is —CH($R_{10}$)—, and $R_{10}$ is heteroaryl (e.g., thienyl).

In some embodiments of formula (III), $X_1$ and $X_2$ are hydrogen, $R_1$ is alkyl (e.g., methyl), and $R_2$ is hydrogen, A is —CH($R_{10}$)—, and $R_{10}$ is heteroaryl (e.g., thienyl).

In some embodiments of formula (III), PG$_\ominus$ is a deprotonated free acid of latanoprost, bimatoprost, travoprost, tafluprost, AR-102, cloprostenol, latanoprostene bunod, unoprostone, PGE$_1$, PGF$_{2\alpha}$ or fluprostenol.

Compounds of formula (III) may be synthesized by combining a prostaglandin free acid and an isoquinoline compound, e.g., in a suitable solvent. The starting materials may be combined in an approximately 1:1 ratio. The mixture may be heated to promote dissolution of the starting materials if necessary. The solvent can then be removed to provide the salt compound.

Prostaglandins and Prostaglandin Analogs

Compositions described herein may include a prostaglandin or a prostaglandin analog.

In some embodiments, a prostaglandin or a prostaglandin analog may comprise a compound of formula (IV):

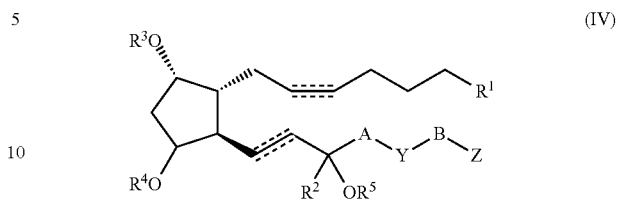

or an optical isomer, diastereomer or enantiomer thereof, wherein:

the dashed lines independently indicate the presence or absence of a bond;

A and B are independently —(CR$^a$R$^b$)$_n$—, wherein each R$^a$ and R$^b$ is independently hydrogen or C$_1$-C$_6$ alkyl, and n is 0, 1, 2, 3 or 4;

R$_1$ is —C(O)OR$^c$, —CONHR$^d$, —C(O)NHOH, —CH$_2$OH, —S(O)$_2$R$^e$ or —C(O)NHS(O)$_2$R$^f$;

R$_2$ is hydrogen or C$_1$-C$_6$ alkyl;

R$_3$, R$^4$ and R$^5$ are independently selected from hydrogen and an alcohol protecting group;

Y is a bond, —O—, —S—, —S(O), —SO$_2$—, —C(R$^g$)$_2$—, —CR$^h$═CR$^i$—, —NR$^j$—, or —C═C—;

Z is hydrogen, cycloalkyl, heterocyclyl, aryl or heteroaryl;

R$^c$ is selected from hydrogen, C$_1$-C$_6$ alkyl, C$_1$-C$_6$ heteroalkyl, aryl, heteroaryl, cycloalkyl and heterocyclyl;

R$^d$, R$^e$ and R$^f$ are independently selected from C$_1$-C$_6$ alkyl, heteroalkyl, aryl, heteroaryl, cycloalkyl and heterocyclyl;

R$^g$, R$^h$ and R$^i$ are independently selected from hydrogen, C$_1$-C$_6$ alkyl, alkoxy and hydroxy; and R$^j$ is hydrogen or C$_1$-C$_6$ alkyl.

Suitably, no carbon atom in a compound of formula (IV) has two or more heteroatoms attached to it unless the two or more heteroatoms are member atoms in a heteroaromatic ring system.

In formula (IV), the relative stereochemistry at C8, C9, and C12 is as specified. That is, the bond between C7 and C8 is in the α orientation, the alcohol (protected or unprotected) at C9 is in the α orientation, and the bond between C12 and C13 is in the β orientation. The invention also includes optical isomers, diastereomers and enantiomers of the above structure. At all stereocenters where stereochemistry is not defined (e.g. C11 and C15), both epimers are envisioned. In some embodiments, stereochemistry at all such stereocenters of the invention mimic that of naturally occurring PGF$_{2\alpha}$.

In some embodiments, Q1 is either H or an alcohol protecting group and Q2 and Q3 are alcohol protecting groups. In other embodiments, Q1, Q2, and Q3 are all alcohol protecting groups and may be different alcohol protecting groups and may be the same alcohol protecting group.

Exemplary prostaglandins and prostaglandin analogs include latanoprost, bimatoprost, travoprost, tafluprost, AR-102, cloprostenol, latanoprostene bunod, unoprostone, PGE$_1$, PGF$_{2\alpha}$ and fluprostenol.

Other prostaglandins and related compounds suitable for use in compositions of the disclosure include, but are not limited to, those found in the following patents and patent applications, which are incorporated herein by reference.

1. 5-Thia-omega substituted phenyl-prostaglandin E derivatives, process for producing the same and drugs containing the same as the active ingredient. WO 00/3980.
2. Aromatic $C_{16}$-$C_{20}$-substituted tetrahydro prostaglandins useful as FP agonists WO 99/12895; U.S. Pat. No. 5,977,173, Nov. 2, 1999.
3. Aromatic C16-C20-substituted tetrahydro prostaglandins useful as FP agonists WO 99/12898.
4. Aromatic C16-C20-substituted tetrahydro prostaglandins useful as FP agonists. WO 99/12896, U.S. Pat. No. 6,048,895 Apr. 11, 2000.
5. Prostaglandins of the F series U.S. Pat. No. 5,770,759. Jun. 23, 1998.
6. EP2-receptor agonists as neuroprotective agents for the eye WO 99/26629.
7. Prostaglandin derivatives for the treatment of glaucoma or ocular hypertension. U.S. Pat. No. 6,030,999, Feb. 29, 2000.
8. Cyclopentane heptan(ene)oic acid, 2-heteroarylalkenyl derivatives as therapeutic agents WO 99/25358; U.S. Pat. No. 6,037,364 Mar. 14, 2000.
9. Use of cloprostenol and fluprostenol analogues to treat glaucoma and ocular hypertension U.S. Pat. No. 5,889,052, Mar. 30, 1999.
10. Cis-delta-4-analogs of prostaglandins as ocular hypotensives. WO 98/21182; U.S. Pat. No. 5,994,397 Nov. 30, 1999.
11. Tetrahydrofuran analogs of prostaglandins as ocular hypotensives. WO 98/57930; U.S. Pat. No. 6,025,392 Mar. 14, 2000.
12. Conformationally rigid aryl- or heteroaryl prostaglandins for use in glaucoma therapy. WO 98/21180.
13. Keto-substituted tetrahydrofuran analogs of prostaglandins as ocular hypotensives WO 98/57930.
14. 13-oxa prostaglandins for the treatment of glaucoma and ocular hypertension WO 99/32441.
15. 13-Thia prostaglandins for use in glaucoma therapy WO 98/39293.
16. 15-Ketal prostaglandins for the treatment of glaucoma or ocular hypertension WO 98/20881.
17. 9-Oxa prostaglandin analogs as ocular hypotensives. WO 98/57942.
18. 15-Fluoro prostaglandins as ocular hypotensives WO 98/21181.
19. 11-Halo prostaglandins for the treatment of glaucoma or ocular hypertension WO 98/20880.
20. Use of 9-deoxy prostaglandin derivatives to treat glaucoma WO 96/10407.
21. Prostaglandin product WO 00/3736.
22. Substituted tetrahydrofuran analogs of prostaglandins as ocular hypotensives WO 97/23223.
23. EP2-receptor agonists as agents for lowering intraocular pressure WO 95/19964.
24. Prostaglandin derivatives devoid of side-effects for the treatment of glaucoma. WO 99/02165.
25. 8-Iso prostaglandins for glaucoma therapy WO 98/50024; U.S. Pat. No. 6,037,368 Mar. 14, 2000.
26. Fluorinated prostaglandin derivatives and medicines WO 98/12175.

Isomers

Compounds described herein (e.g., compounds of formula (I), (Ia), (Ib), (II), (III) and (IV)) may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; a- and β-forms; axial and equatorial forms; boat-, chair-, twist-, envelope-, and half chair-forms; and combinations thereof, hereinafter collectively referred to as "isomers" (or "isomeric forms").

In one embodiment, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_3$-alkyl or propyl includes n-propyl and iso-propyl; $C_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Salts

A compound described herein can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." *J. Pharm. Sci.* Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations. Examples of suitable organic cations include, but are not limited to, ammonium ion (i.e., NH$_4^+$) and substituted ammonium ions (e.g., NH$_3$R$_1^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Chemically Protected Forms

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)CH$_3$, —OAc).

An aldehyde or ketone group may be protected as an acetal (RCH(OR)$_2$) or ketal (R$_2$C(OR)$_2$), respectively, in which the carbonyl group (R$_2$C═O) is converted to a diether (R$_2$C(OR)$_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—NHC(O)CH$_3$); a benzyloxy amide (—NHC(O)OCH$_2$C$_6$H$_5$, —NH-Cbz); as a t-butoxy amide (—NHC(O)OC(CH$_3$)$_3$, —NH-Boc); a 2-biphenyl-2-propoxy amide (—NHCO(O)C(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH—Teoc), as a 2,2,2-trichloroethyloxy amide (—NH-Troc), as an allyloxy amide (—NH—Alloc), as a 2(-phenylsulphonyl)ethyloxy amide (—NH—Psec); or, in suitable cases (e.g., cyclic amines), as a nitroxide radical (>N-0<<).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—CH$_2$NHC(O)CH$_3$)

Prodrugs and Other Modifications

In addition to salt forms, the present invention may also provide compounds that are in a prodrug form. Prodrugs of the compounds described herein are those compounds that readily undergo chemical changes under physiological conditions to provide the compounds described herein. Prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

Compositions

In one aspect, the disclosure provides a composition comprising a compound of formula (I) as described herein (e.g., a compound of formula (I), a compound of formula (Ia), or a compound of formula (Ib)), and a prostaglandin or a prostaglandin analog (e.g., a compound of formula (IV)). In another aspect, the disclosure may provide a composition comprising 2-(dimethylamino)-N-(1-hydroxyisoquinolin-6-yl)-2-(thiophen-3-yl)acetamide hydrochloride (e.g., the racemic compound or the (R) or (S) enantiomer), and a compound selected from the group consisting of latanoprost, bimatoprost, travoprost, tafluprost, AR-102, cloprostenol, latanoprostene bunod, unoprostone, PGF$_{2\alpha}$ and fluprostenol. In another aspect, the disclosure may provide a composition comprising 4-(3-amino-1-(isoquinolin-6-ylamino)-1-oxopropan-2-yl)benzyl 2,4-dimethylbenzoate (e.g., the racemic compound or the (R) or (S) enantiomer), and a compound selected from the group consisting of latanoprost, bimatoprost, travoprost, tafluprost, AR-102, cloprostenol, latanoprostene bunod, unoprostone, PGF$_{2\alpha}$ and fluprostenol. In another aspect, the disclosure provides a composition comprising a compound of formula (II) as described herein. In another aspect, the disclosure provides a composition comprising a compound of formula (III) as described herein.

Compositions of the present disclosure may comprise safe and effective amounts of the subject compounds. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of treatment, the nature of concurrent therapy, the particular pharmaceutically-acceptable carrier utilized, and like factors within the knowledge and expertise of the attending physician.

In embodiments, a composition may include a compound of formula (I), (Ia), (Ib), (II) or (III) at an amount of about 0.001% to about 2.0% w/v, e.g., about 0.01% to about 1.0% w/v. In embodiments, a compound of formula (I), (Ia), (Ib), (II) or (III) may be included in a composition at an amount of less than about 0.0025%, less than about 0.010%, less than about 0.015%, less than about 0.025%, less than about 0.05%, less than about 0.080%, less than about 0.10%, less than about 0.20%, less than about 0.40%, less than about 0.60%, less than about 0.80%, less than about 0.10%, less than about 0.5%, less than about 0.7%, less than about 1.0%, less than about 1.2%, less than about 1.4%, less than about 1.5%, less than about 1.6%, less than about 1.8, less than about 2.0%, at least about 0.0025%, at least about 0.010%, at least about 0.015%, at least about 0.020%, at least about 0.05%, at least about 0.075%, at least about 0.10%, at least about 0.20%, at least about 0.40%, at least about 0.60%, at least about 0.80, at least about 1.0%, at least about 1.2%, at least about 1.4%, at least about 1.6%, at least about 1.8%, at least about 2.0, about 0.0025%, about 0.010%, about 0.015%, about 0.03%, about 0.05%, about 0.10%, about 0.20%, about 0.40%, about 0.60%, about 0.80%, about 1.0%, about 1.2%, about 1.4%, about 1.6%, about 1.8%, or about 2.0%.

In embodiments, a composition may include a prostaglandin or a prostaglandin analog (e.g., a compound of formula (IV), or latanoprost, bimatoprost, travoprost, tafluprost, AR-102, cloprostenol, latanoprostene bunod, unoprostone, PGF$_{2\alpha}$ or fluprostenol) at an amount of about 0.0001% to about 0.5% w/v, e.g., about 0.0005% to about 0.1% w/v, or about 0.001% to about 0.05%. In embodiments, a prostaglandin or prostaglandin analog may be included in a composition at an amount of about 0.001%, about 0.002%, about 0.003%, about 0.004%, about 0.005%, about 0.006%, about 0.007%, about 0.008%, about 0.009%, about 0.010%, about 0.011%, about 0.012%, about 0.013%, about 0.014%, about 0.015%, about 0.016%, about 0.017%, about 0.018%, about 0.019%, about 0.020%, about 0.021%, about 0.022%, about 0.023%, about 0.024%, about 0.025%, about 0.026%, about 0.027%, about 0.028%, about 0.029%, about 0.030%, about 0.031%, about 0.032%, about 0.033%, about 0.034%, about 0.035%, about 0.036%, about 0.037%, about 0.038%, about 0.039%, about 0.040%, about 0.041%, about 0.042%, about 0.043%, about 0.044%, about 0.045%, about 0.046%, about 0.047%, about 0.048%, about 0.049%, or about 0.050%.

Additional Components

Compositions of the present disclosure may further include one or more pharmaceutically acceptable excipients. For example, compositions may include additional, pharmaceutically acceptable components such as buffers, tonicity agents, chelating agents, sugars or sugar alcohols, viscosity enhancers and surfactants.

A buffer may comprise, for example, phosphate buffer, borate buffer, citrate buffer, maleate buffer, tartrate buffer, acetate buffer, tris(hydroxymethyl)aminomethane (TRIS), an amino acid buffer (e.g., glycine), combination buffers such as borate/phosphate buffer, citrate/phosphate buffer, and the like. In embodiments, a composition may include an amount of a buffer that is effective to provide a suitable buffering capacity to a composition. Other components of the compositions, while having other functions, may also affect the buffer capacity. For example, ethylenediaminetetraacetic acid (EDTA), often used as a chelating agent, can have an effect on the buffer capacity of a solution.

Compositions may include one or more tonicity agents, such that the composition may be isotonic with body fluids. A tonicity agent can be non-ionic or ionic. Non-ionic tonicity agents include sugars, sugar alcohols and other polyols, diols such as glycerol, mannitol, erythritol, and sugars such as dextrose. Other non-ionic tonicity agents such as polyethylene glycols, propylene glycol, which also function as co-solvents, can also be used. A tonicity agent can also be an ionic agent such as, for example, sodium chloride, potassium chloride, a balanced salt solution, sodium phosphate, or sodium citrate. For example, a non-ionic tonicity agent may be included in a composition at an amount of about 0.10 to about 20%, about 1.0 to about 10%, or about 2.0 to about 6.0%. An ionic tonicity agent may be included in a composition at an amount of about 0.10% to about 2.5%, about 0.25% to about 2.0%, or about 0.50% to about 1.0% w/v.

Compositions may also include one or more chelating agents or sequestering agents. A wide range of organic acids, amines or compounds which include an acid group and an amine function are capable of acting as chelating agents. For example, nitrilotriacetic acid, diethylenetriaminepentacetic acid, hydroxyethylethylenediaminetriacetic acid, 1,2-diaminocyclohexane tetraacetic acid, hydroxyethylaminodiacetic acid, ethylenediaminetetraacetic acid and its salts, polyphosphates, citric acid and its salts, tartaric acid and its salts, and the like and mixtures thereof, are useful as chelating agents. Ethylenediaminetetraacetic acid (EDTA) and its alkali metal salts, are suitable chelating agents, such as the disodium salt of EDTA (also known as disodium edetate). In embodiments, a chelating agent may be included in a composition at an amount of about 0.001% to about 0.25% w/v, about 0.005% to about 0.15% w/v, or about 0.01% to about 0.1% w/v. In embodiments, a composition may include a chelating agent in an amount effective to enhance the effectiveness of an antimicrobial component and/or to complex with metal ions.

Compositions may further include one or more preservatives. Suitable preservatives include, but are not limited to, sodium bisulfate, sodium bisulfate, sodium thiosulfate, ascorbate, benzalkonium chloride, benzododecinium bromide, chlorobutanol, thimerosal, phenylmercuric acetate, phenylmercuric borate, phenylmercuric nitrate, parabens such as methylparaben, ethylparaben and propylparaben, polyvinyl alcohol, benzyl alcohol, phenylethanol, sodium benzoate, sorbic acid, polyquaternium-1, and the like and mixtures thereof. In embodiments, a composition may include a preservative in amounts of 0.001 to about 1% or about 0.005 to about 0.10% w/v. In embodiments, a composition may include a preservative in an amount that is effective to inhibit microbial growth or contamination of the composition.

Compositions may additionally include a surfactant. Surfactants include non-ionic, anionic, amphoteric and zwitterionic surfactants. Exemplary surfactants include but are not limited to sodium lauryl sulfate, polyethoxylated sorbitan fatty acid esters, polyoxyethylene alkyl ethers, polyoxyethylene stearates (e.g., polyoxyethylene(40) stearate such as Myrj™-52), poloxamers, polaxamines, sorbitan fatty acid esters, polyethylene glycols (e.g., PEG-400), polyethoxylated alcohols, polyethoxylated castor oils (e.g., PEG-40 hydrogenated castor oil, such as Cremophor® RH 40), docusate sodium, quaternary ammonium compounds, medium and long chain fatty acids, sugar esters of fatty acids and glycerides of fatty acids, lecithin, polysorbate 80, phospholipids and sodium lauryl sulfate. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. Surfactants may be included in compositions at amounts of about 0.01% to about 5%, or about 0.1% to about 2% w/v.

Compositions may also include a viscosity enhancer, which may increase the resident time of a composition on the ocular surface. Exemplary viscosity enhancers include but are not limited to water soluble natural gums, cellulose-derived polymers and the like. Suitable natural gums include guar gum, gum tragacanth and the like. Suitable cellulose-derived viscosity inducing components include cellulose-derived polymers, such as sodium carboxymethylcellulose, hydroxypropyl cellulose, hydroxypropylmethyl cellulose, carboxymethyl cellulose, methyl cellulose, ethyl cellulose, hydroxyethyl cellulose and the like. Viscosity enhancers may be included in compositions at amounts of about 0.01% to about 5%, or about 0.1% to about 3% w/v.

Compositions described herein may also include a solvent. Compositions are typically aqueous, but may also include optional co-solvents. Suitable co-solvents include but are not limited to alcohols such as ethanol and isopropanol, ethylene glycol monoethyl ether, diethylene glycol monobutyl ether, diethylene glycol monoethyl ether, dimethylsulfoxide, dimethyl formamide, castor oil and combinations thereof. In addition to a compound of formula (I) or (II) a prostaglandin, and other optional components, the balance of a composition may comprise solvent.

pH

The pH of compositions can affect both stability of the compound and efficacy. For example, higher pH may result in decomposition of a compound of formula (I), while lower pH may be irritating to the eye. In embodiments the pH may be about 4.0 to about 7.0, or about 5.0 to about 6.0. In embodiments, a composition may have a pH of at least about 5.0, at least about 5.5, at least about 6.0, at least about 6.5, at least about 7.0, less than about 5.0, less than about 5.5, less than about 6.0, less than about 6.5, less than about 7.0, about 5.0, about 5.1, about 5.2, about 5.3, about 5.4, about 5.5, about 5.6, about 5.7, about 5.8, about 5.9, or about 6.0.

Composition pH can be adjusted with acid or base, if necessary. Any acid or base compatible with the components of the composition can be used. Exemplary acids include hydrochloric acid, citric acid, gluconic acid, lactic acid, acetic acid, and glycolic acid. Exemplary bases include sodium hydroxide, potassium hydroxide, and triethanolamine.

Methods of Making Compositions

Compositions may be prepared using standard methods. In embodiments, composition components may be combined in water (e.g., purified water) with stirring, followed by pH adjustment to a suitable final pH. Techniques for preparing compositions may generally be found in "Remington's Pharmaceutical Sciences", (Meade Publishing Co., Easton, Pa.).

When preparing compositions, components should be selected to optimize solubility, stability and compatibility. Compositions should typically be sterile and stable under the conditions of manufacture and storage. Compositions may be sterilized by filtering the composition through a sterilizing grade filter, such as a filter with a 0.22 micron nominal pore size.

Methods of Evaluating Compositions

Compositions may be evaluated for stability using established procedures. For example, compositions may be subjected to accelerated stability testing. For example, compositions remain stable, and do not undergo precipitation or become cloudy when they are stored at 40° C. for at least 1 month, 3 months or 6 months prior to evaluation. The active component (e.g., a 6- or 7-aminoisoquinoline compound) should not react with other formulation components, or decompose. Methods of evaluating such compounds include, for example, high performance liquid chromatography (HPLC) or determination of optical rotation (e.g., to determine if a compound has racemized).

Compositions may also be evaluated using the Preservative Effectiveness Test of the United States Pharmacopoeia for parenteral/ophthalmic products. In such tests, which will be known to those skilled in the art, five indicator organisms are utilized for the purpose of challenging the preservative system in a product. Three of the five USP indicator organisms address the growth of bacteria: *Escherichia coli, Pseudomonas aeruginosa*, and *Staphylococcus aureus*. *Candida albicans* is the representative yeast, while *Aspergillus niger* is a mold. A product is inoculated (contaminated) with a number of organisms between $1\times10^5$ (100,000) to $1\times10^6$ (1,000,000) colony forming units (CFU) per mL of product. At various intervals, depending on the category, the composition is tested to determine its ability to control reproduction or destroy the microorganisms. A logarithmic reduction is evaluated at each test interval required for the category. By test definition, any growth over the allotted amount for any of the indicated microorganisms renders the preservative in the product not effective. Compositions may also be evaluated using the European Pharmacopoeia Preservative Effectiveness Test, which also evaluates growth of *P. aeruginosa, S. aureus, C. albicans* and *A. niger*. The compositions of the present disclosure will pass at least one of these preservative effectiveness tests.

Pharmacological activity for glaucoma can be demonstrated using assays designed to test the ability of the subject compounds to decrease intraocular pressure. Examples of such assays are described in the following paper, incorporated herein by reference: C. Liljebris, G. Selen, B. Resul, J. Sternschantz, and U. Hacksell, "Derivatives of 17-Phenyl-18,19,20-trinorprostaglandin $F_{2\alpha}$ Isopropyl Ester: Potential Anti-glaucoma Agents", *Journal of Medicinal Chemistry*, Vol. 38 (2) 1995, pp. 289-304. Further methods are described in the Examples.

Methods of Use

One aspect of the disclosure relates to a method of treating an ocular disorder in a subject in need of treatment, comprising administering to the subject a safe and effective amount of a composition comprising an isoquinoline compound such as a compound of formula (I), and a prostaglandin or a prostaglandin analog. Another embodiment includes a method of treating an ocular disorder in a subject in need of treatment, comprising administering to the subject a safe and effective amount of a composition comprising a compound of formula (II). Another embodiment of the disclosure includes a method of reducing intraocular pressure comprising administering to a subject in need thereof a safe and effective amount of a composition comprising an isoquinoline compound such as a compound of formula (I), and a prostaglandin or a prostaglandin analog. Another embodiment includes a method of reducing intraocular pressure comprising administering to a subject in need thereof a safe and effective amount of a composition comprising a compound of formula (II).

The compounds of formula (I) and (II) and compositions including them may have kinase inhibitory activity and are thus useful in influencing or inhibiting the action of kinases, and in treatment and/or prevention of diseases or conditions influenced by kinases. Exemplary kinases that may be influenced include, but are not limited to, ROCK-I, ROCK-II, PKA, PKC, CAM Kinases, GRK-2, GRK-3, GRK-5 or GRK-6. In a suitable embodiment, the kinase inhibited is a Rho-associated protein kinase.

In embodiments, the compositions of the present disclosure may be topically administered. Topical compositions that can be applied locally to the eye may be in any form known in the art, non-limiting examples of which include drops, sprays, ointments, or a sustained or non-sustained release unit placed in the conjunctival cul-du-sac of the eye or another appropriate location.

Dosages may be varied based on the patient being treated, the condition being treated, the severity of the condition being treated, the route of administration, etc. to achieve the desired effect.

Administration of a compound or a composition described herein may result in a decrease in intraocular pressure (IOP) of at least about 3.0 mmHg, at least about 3.5 mmHg, at least about 4.0 mmHg, at least about 4.5 mmHg, at least about 5.0 mmHg, at least about 5.5 mmHg, at least about 6.0 mmHg, at least about 6.5 mmHg, at least about 7.0 mmHg, at least about 7.5 mmHg, at least about 8.0 mmHg, at least about 8.5 mmHg, at least about 9.0 mmHg, at least about 9.5 mmHg, at least about 10.0 mmHg, about 3.0 mmHg, about 3.5 mmHg, about 4.0 mmHg, about 4.5 mmHg, about 5.0 mmHg, about 5.5 mmHg, about 6.0 mmHg, about 6.5 mmHg, about 7.0 mmHg, about 7.5 mmHg, about 8.0 mmHg, about 8.5 mmHg, about 9.0 mmHg, about 9.5 mmHg, or about 10.0 mmHg. In some embodiments, administration of a composition comprising a compound of formula (I) and a prostaglandin or prostaglandin analog may reduce intraocular pressure more than either single compound alone, or more than intraocular pressure is reduced when both compounds are administered to a subject in separate compositions.

The following examples are intended to be illustrative, and should be considered to be non-limiting.

EXAMPLES

Example 1. Formulations with Travoprost

Topical pharmaceutical compositions for lowering intraocular pressure were prepared by conventional methods and formulated as follows:

| | Formulation | | | |
|---|---|---|---|---|
| | 1 (% w/w) | 2 (% w/w) | 3 (% w/w) | 4 (% w/w) |
| (rac)-2-(dimethylamino)-N-(1-hydroxyisoquinolin-6-yl)-2-(thiophen-3-yl)acetamide hydrochloride | 0.5 | 0.5 | 0.25 | 0.5 |
| Travoprost | 0.004 | 0.004 | 0.004 | 0.004 |
| Boric acid | 0.05 | 0.05 | 0.05 | 0.05 |
| D-mannitol | 3.0 | 3.0 | 3.0 | 3.0 |
| Benzalkonium chloride | 0.015 | 0.015 | 0.015 | — |
| Polyoxyl 40 stearate (Myrj-52) | 0.5 | — | 0.5 | 0.5 |
| Cremophor RH 40 | — | 0.5 | — | — |

-continued

|  | Formulation | | | |
|---|---|---|---|---|
|  | 1 (% w/w) | 2 (% w/w) | 3 (% w/w) | 4 (% w/w) |
| Polyethylene glycol 400 (PEG-400) | 2.5 | 2.5 | 2.5 | 2.5 |
| EDTA | 0.01 | 0.01 | 0.01 | 0.01 |
| Purified water | q.s. | q.s. | q.s. | q.s. |

Formulations 1-3 were prepared by adding boric acid, D-mannitol, PEG-400, EDTA, and Myrj-52 or Cremophor RH40 in a labeled 150-milliliter (mL) plastic container. 100 milliliters (mL) of purified water were then added to bring the solution almost to 100%. The solution was stirred for 10 minutes. Stock solutions of 1.5% benzalkonium chloride, 0.4% travoprost, and (rac)-2-(dimethylamino)-N-(1-hydroxyisoquinolin-6-yl)-2-(thiophen-3-yl)acetamide hydrochloride were then added and dissolved by stirring the solution for another 10 minutes, and the pH was adjusted to approximately 5.5.

Formulation 4 was prepared by adding boric acid, D-mannitol, PEG-400, EDTA, and Myrj-52 or Cremophor RH40 in a labeled 150-mL plastic container. 100 mL purified water was then added to bring the solution almost to 100%. The solution was stirred for 10 minutes. (R)-2-(dimethylamino)-N-(1-hydroxyisoquinolin-6-yl)-2-(thiophen-3-yl)acetamide hydrochloride and travoprost were then added and dissolved by stirring the solution for another 10 minutes, and the pH was adjusted to approximately 5.5.

Formulation 1 passed the requirements of the United States Pharmacopoeia Preservative Effectiveness Test for parenteral/ophthalmic products (USP), the European Pharmacopoeia Preservative Effectiveness Test (EP-A) and the European Pharmacopoeia Preservative Effectiveness Test (EP-B).

Example 2. Formulations with Latanoprost

Topical pharmaceutical compositions for lowering intraocular pressure were prepared by conventional methods and formulated as follows:

|  | Formulation | |
|---|---|---|
|  | 5 (% w/w) | 6 (% w/w) |
| (rac)-2-(dimethylamino)-N-(1-hydroxyisoquinolin-6-yl)-2-(thiophen-3-yl)acetamide hydrochloride | 0.5 | 0.7 |
| Latanoprost | 0.005 | 0.005 |
| Sodium Phosphate Monobasic | 0.031 | 0.0155 |
| Sodium Phosphate Dibasic | 0.07 | 0.0035 |
| Benzalkonium chloride | 0.015 | 0.015 |
| sodium chloride | 0.7 | 0.7 |
| EDTA | 0.05 | 0.05 |
| Purified water | q.s. | q.s. |

Formulations 5 and 6 were prepared by adding sodium phosphate monobasic, sodium phosphate dibasic, sodium chloride, and EDTA in a labeled 150-milliliter (mL) plastic storage container. 100 milliliter (mL) of purified water was then added to bring the solution almost to 100%. The solution was stirred for 10 minutes. Stock solutions of 1.5% benzalkonium chloride, and 0.5% latanoprost, and (rac)-2-(dimethylamino)-N-(1-hydroxyisoquinolin-6-yl)-2-(thiophen-3-yl)acetamide hydrochloride were then added and dissolved by stirring the solution for another 10 minutes, and the pH was adjusted to approximately 5.5.

|  | Formulation | |
|---|---|---|
|  | 7 (% w/w) | 8 (% w/w) |
| (rac)-2-(dimethylamino)-N-(1-hydroxyisoquinolin-6-yl)-2-(thiophen-3-yl)acetamide hydrochloride | 0.5 | 0.7 |
| Latanoprost | 0.005 | 0.005 |
| Boric acid | 0.05 | 0.05 |
| D-mannitol | 4.3 | 4.0 |
| Benzalkonium chloride | 0.015 | 0.015 |
| EDTA | 0.01 | 0.01 |
| Purified water | q.s. | q.s. |

Formulations 7 and 8 were prepared by adding boric acid, D-mannitol, and EDTA in a labeled 150-milliliter (mL) plastic container. 100 milliliter (mL) of purified water was then added to bring the solution almost to 100%. The solution was stirred for 10 minutes. Stock solutions of 1.5% benzalkonium chloride, 0.5% travoprost, and (rac)-2-(dimethylamino)-N-(1-hydroxyisoquinolin-6-yl)-2-(thiophen-3-yl)acetamide hydrochloride were then added and dissolved by stirring the solution for another 10 minutes, and the pH was adjusted to approximately 5.5.

Example 3. Formulations with Bimatoprost

Topical pharmaceutical compositions for lowering intraocular pressure were prepared by conventional methods and formulated as follows:

|  | Formulation | | |
|---|---|---|---|
|  | 9 (% w/w) | 10 (% w/w) | 11 (% w/w) |
| (rac)-2-(dimethylamino)-N-(1-hydroxyisoquinolin-6-yl)-2-(thiophen-3-yl)acetamide hydrochloride | 0.5 | 0.5 | 0.5 |
| Bimatoprost | 0.03 | 0.01 | 0.03 |
| Boric acid | — | — | 0.05 |
| D-mannitol | — | — | 4.3 |
| Sodium Phosphate Monobasic | 0.31 | 0.31 | — |
| Sodium Phosphate Dibasic | 0.07 | 0.07 | — |
| Benzalkonium chloride | 0.0075 | 0.02 | — |
| Sodium chloride | 0.7 | 0.7 | — |
| EDTA | 0.05 | 0.05 | — |
| Purified water | q.s. | q.s. | q.s. |

Formulations 9 and 10 were prepared by adding sodium phosphate monobasic, sodium phosphate dibasic, sodium chloride, and EDTA in a labeled 150-milliliter (mL) plastic storage container. 100 milliliter (mL) of purified water was then added to bring the solution almost to 100%. The solution was stirred for 10 minutes. 1.5% stock solution of benzalkonium chloride, bimatoprost, and (rac)-2-(dimethylamino)-N-(1-hydroxyisoquinolin-6-yl)-2-(thiophen-3-yl)acetamide hydrochloride were then added and dissolved by stirring the solution for another 10 minutes, and the pH was adjusted to approximately 5.5.

Formulation 11 was prepared by adding boric acid and D-mannitol in a labeled 150-milliliter (mL) plastic storage container. 100 milliliter (mL) of purified water was then added to bring the solution almost to 100%. The solution was stirred for 10 minutes. Bimatoprost and (rac)-2-(dimethylamino)-N-(1-hydroxyisoquinolin-6-yl)-2-(thiophen-3-yl)acetamide hydrochloride were then added and dissolved by stirring the solution for another 10 minutes, and the pH was adjusted to approximately 5.5.

Example 4. Exemplary Combination Treatment

Formosan Rock monkeys (*Macaca cyclopis*), animal identification consisting of uniquely numbered tattoos and color-coded cage cards were used in this study. On Study Day 1, the animals were at least four years old, and weighed at least 4 kg. The ocular hypotensive efficacy and tolerability were determined using a paired study design in which composition was administered q.d. AM for three days to one eye of each monkey (n=6 per group) with the untreated contralateral eye serving as an internal control. Each dose was administered just after the t=0, t=24, and t=48 hour measurement of intraocular pressure (IOP). IOP was taken in both eyes at time points of 0, 4, 8, 24, 48, 52, 56, and 72 hours after baseline (t=0) IOP measurement. Mortality observations, clinical observations, ocular irritation, and intraocular pressures were monitored, recorded, or measured throughout the in-life portion of the study. All treatments were administered as eye drops (one drop per eye). Each animal was sedated intramuscularly (IM) with approximately 5 mg/kg ketamine HCl (or to effect) with the objective of using the minimal dose necessary to achieve acceptable sedation to perform the IOP measurement and dosing procedure. A Model 30 Classic™ pneumatonometer was used to measure intraocular pressure (IOP) non-invasively (Reichert, Inc, Depew, N.Y.). One drop of ocular anaesthetic (0.5% proparacaine) was topically applied to each eye and allowed to take effect for at least 30 seconds prior to each IOP measurement. Using the pneumatonometer manual tonometry mode, and with the animal maintained in an upright position, 3 independent measurements were obtained and averaged for each eye, at all time points.

Three Rho Kinase inhibitor (ROCKi) formulations were prepared by dissolving 0.5% ROCKi (rac)-2-(dimethylamino)-N-(1-hydroxyisoquinolin-6-yl)-2-(thiophen-3-yl)acetamide hydrochloride directly in the commercially-used formulations of 0.004% travoprost (Travatan® Z), 0.005% latanoprost (Xalatan) and 0.01% bimatoprost (Lumigan), with adjustment of the final pH to 5.5. When tested according to the above protocol, significant IOP reductions were observed for each combination above what the components would do individually. Results are illustrated graphically in FIG. 1. (Data for individual compounds are not shown for clarity.)

Example 5. Synergistic Combination Treatment

Topical pharmaceutical compositions for lowering intraocular pressure were prepared by conventional methods and formulated as follows:

| | Formulation | |
|---|---|---|
| | 12 | 13 |
| (S)-4-(3-amino-1-(isoquinolin-6-ylamino)-1-oxopropan-2-yl)benzyl 2,4-dimethylbenzoate | 0.02 | 0.02 |
| Travoprost | — | 0.004 |
| Boric acid | 0.05 | 0.05 |
| D-mannitol | 4.7 | 3.5 |
| Benzalkonium chloride | 0.015 | 0.015 |
| Polyoxyl 40 stearate (Myrj-52) | — | 0.5 |
| Polyethylene glycol 400 (PEG-400) | — | 2.5 |
| EDTA | — | 0.01 |
| Purified water | q.s. | q.s. |

Formulation 12 was prepared by adding boric acid, D-mannitol, and EDTA in a labeled 150-mL plastic container. 100 mL purified water was then added to bring the solution almost to 100%. The solution was stirred for 10 minutes. Stock solution of 5% benzalkonium chloride and (S)-4-(3-amino-1-(isoquinolin-6-ylamino)-1-oxopropan-2-yl)benzyl 2,4-dimethylbenzoate were then added and dissolved by stirring the solution for another 10 minutes, and the pH was adjusted to approximately 5.0.

Formulation 13 was prepared by adding boric acid, D-mannitol, PEG-400, EDTA, and Myrj-52 in a labeled 150-mL plastic container. 100 mL purified water was then added to bring the solution almost to 100%. The solution was stirred for 10 minutes. Stock solutions of 1.5% benzalkonium chloride, 0.4% travoprost, and ROCKi (S)-4-(3-amino-1-(isoquinolin-6-ylamino)-1-oxopropan-2-yl)benzyl 2,4-dimethylbenzoate were then added and dissolved by stirring the solution for another 10 minutes, and the pH was adjusted to approximately 5.0.

Figure 2:
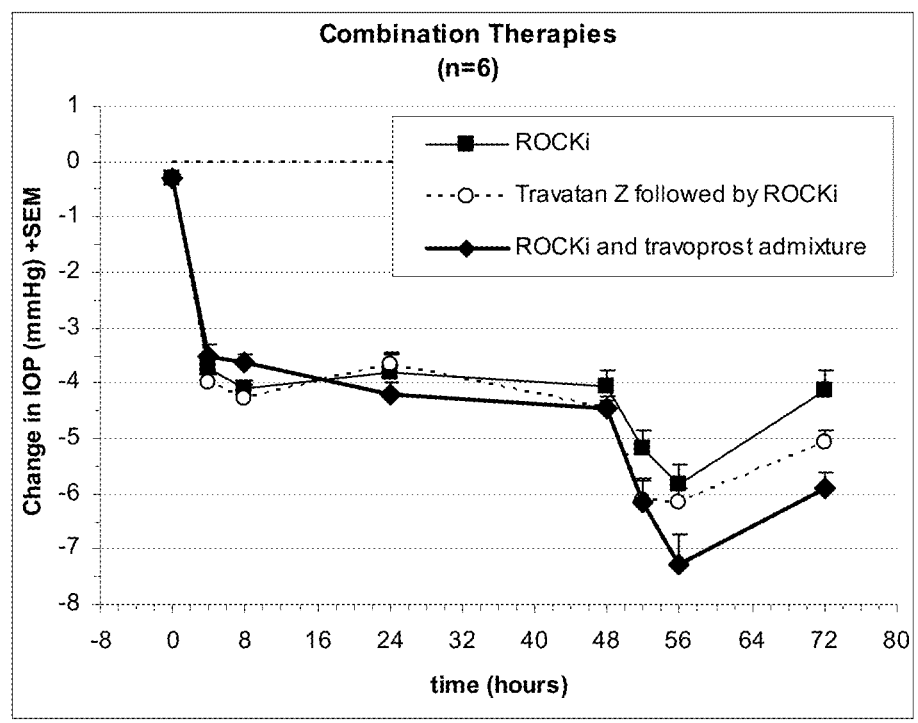
FIG. 2 is a graph showing intraocular pressure following administration of compositions described in Example 5.

For certain topical ophthalmic glaucoma medications, fixed-dose formulations containing mixtures of two compounds have proven to be less effective than concomitant administration of the separate compounds. Using the protocol as described in Example 4, above, an experiment was conducted to see if administering an admixture of a ROCKi and travoprost (Formulation 13) was less effective than concomitant administration of the separate compounds. Surprisingly, not only was there no loss of efficacy with Formulation 13, dosing with the admixture resulted in a substantially better IOP response than concomitant dosing of the two separate compounds (Formulation 12 and Travatan Z). Results are illustrated graphically in FIG. 2.

Example 6. Combination Treatment in Humans

A sterile, isotonic, aqueous solution was prepared, containing (rac)-2-(dimethylamino)-N-(1-hydroxyisoquinolin-6-yl)-2-(thiophen-3-yl)acetamide hydrochloride and travoprost at concentrations of 0.5% and 0.004%, respectively, and the following excipients: Boric Acid (NF), Mannitol (USP), Polyethylene glycol 400 (USP), Polyoxyl 40 Stearate (NF), Edetate Disodium (USP), Water for Injection (USP), and benzalkonium chloride (NF) 0.015% as a preservative. The product may be adjusted with NaOH (USP) and/or HCL (USP) to pH 5.2-5.9.

Using the formulation above, a human diagnosed with elevated intraocular pressure (IOP) was treated once daily with approximately 35 microliter drop(s) in both eyes for up to 28 days. Following this dosing regimen, a measurement of IOP showed a significant reduction from baseline.

Example 7. Synthesis of ROCKi-Latanoprost Conjugate
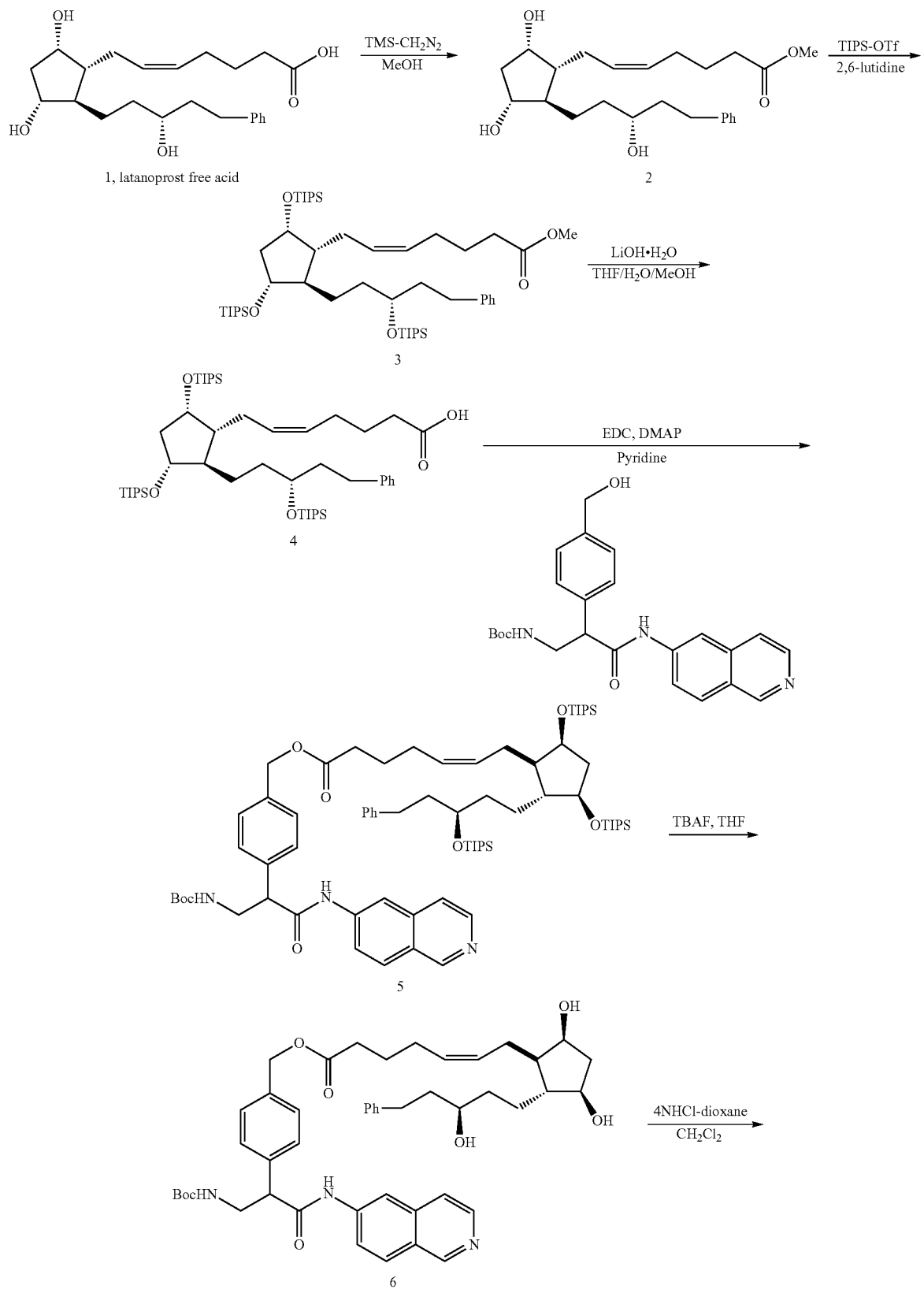

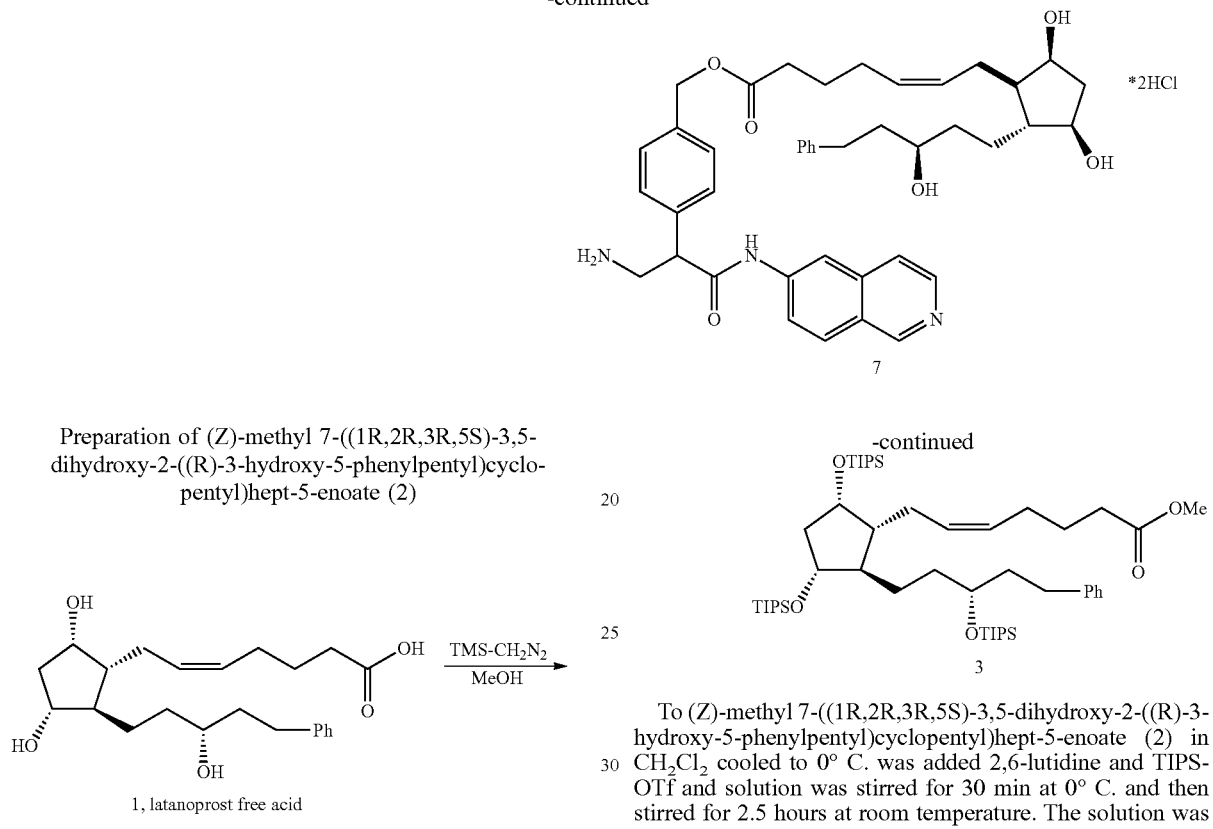

Preparation of (Z)-methyl 7-((1R,2R,3R,5S)-3,5-dihydroxy-2-((R)-3-hydroxy-5-phenylpentyl)cyclopentyl)hept-5-enoate (2)

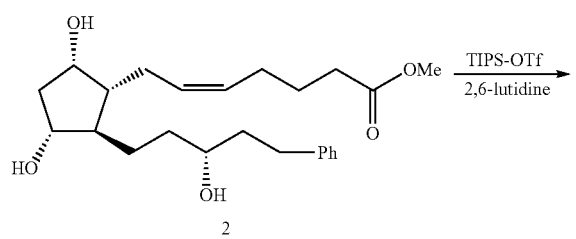

To Latanoprost free acid in MeOH at 0° C. was added TMS-CH$_2$N$_2$ until the solution persisted a yellow color. AcOH (2 drops) were added to quench excess TMS-CH$_2$N$_2$ and the solvents were evaporated. Column chromatography 70%-100% EtOAc/Hexanes gave pure (Z)-methyl 7-((1R,2R,3R,5S)-3,5-dihydroxy-2-((R)-3-hydroxy-5-phenylpentyl)cyclopentyl)hept-5-enoate (2).

Preparation of (Z)-methyl 7-((1R,2R,3R,5S)-2-((R)-5-phenyl-3-(triisopropylsilyloxy)pentyl)-3,5-bis(triisopropylsilyloxy)cyclopentyl)hept-5-enoate (3)

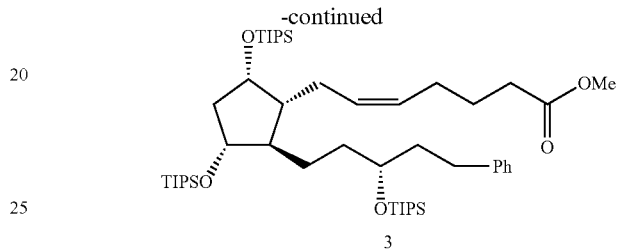

To (Z)-methyl 7-((1R,2R,3R,5S)-3,5-dihydroxy-2-((R)-3-hydroxy-5-phenylpentyl)cyclopentyl)hept-5-enoate (2) in CH$_2$Cl$_2$ cooled to 0° C. was added 2,6-lutidine and TIPS-OTf and solution was stirred for 30 min at 0° C. and then stirred for 2.5 hours at room temperature. The solution was poured into EtOAc and NH$_4$Cl(sat)/HCl (1 N) (3:1) and further extracted with EtOAc. The organics were dried (Na$_2$SO$_4$), filtered and evaporated. Column chromatography 10% EtOAc/Hexanes gave (Z)-methyl 7-((1R,2R,3R,5S)-2-((R)-5-phenyl-3-(triisopropylsilyloxy)pentyl)-3,5-bis(triisopropylsilyloxy)cyclopentyl)hept-5-enoate (3).

Preparation of (Z)-7-((1R,2R,3R,5S)-2-((R)-5-phenyl-3-(triisopropylsilyloxy)pentyl)-3,5-bis(triisopropylsilyloxy)cyclopentyl)hept-5-enoic acid (4)

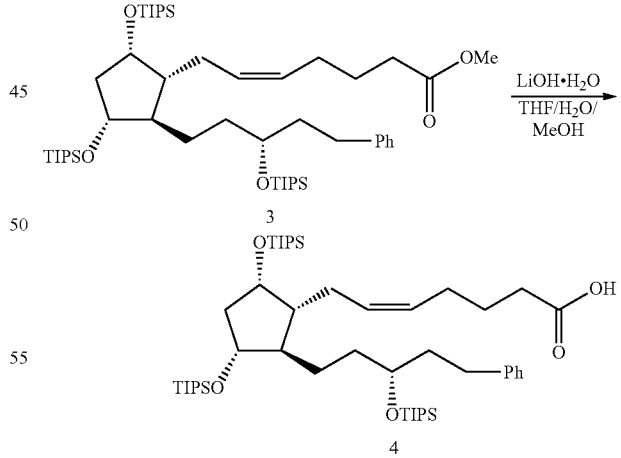

To 3 in THF/MeOH/H$_2$O was added LiOH*H$_2$O and the solution was stirred overnight at room temperature. The solution was poured into EtOAc and NH$_4$Cl(sat)/HCl (1 N) (3:1) and further extracted with EtOAc. The organics were dried (Na$_2$SO$_4$), filtered and evaporated to give (Z)-7-((1R,2R,3R,5)-2-((R)-5-phenyl-3-(triisopropylsilyloxy)pentyl)-3,5-bis(triisopropylsilyloxy)cyclopentyl)hept-5-enoic acid (4).

Preparation of (Z)-4-(3-(tert-butoxycarbonylamino)-1-(isoquinolin-6-ylamino)-1-oxopropan-2-yl)benzyl 7-((1R,2R,3R,5S)-2-((R)-5-phenyl-3-(triisopropylsilyloxy)pentyl)-3,5-bis(triisopropylsilyloxy)cyclopentyl)hept-5-enoate (5)

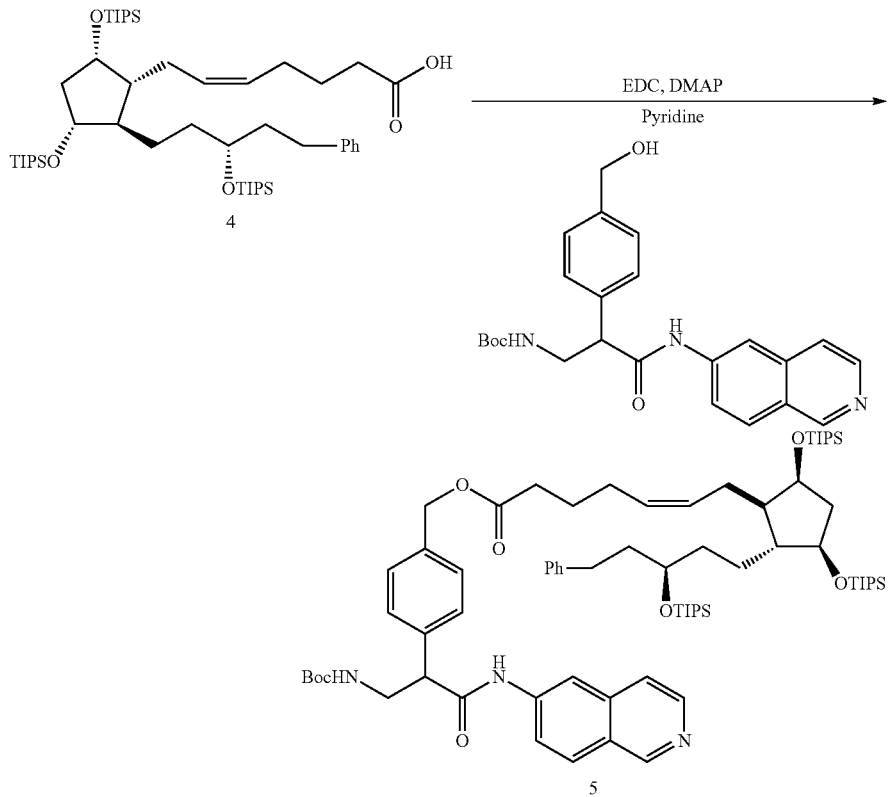

To 4 in pyridine was added tert-butyl 2-(4-(hydroxymethyl)phenyl)-3-(isoquinolin-6-ylamino)-3-oxopropylcarbamate, EDC, and DMAP and the solution was flushed with Argon, capped and stirred overnight. The mixture as poured into NaHCO₃(sat) and extracted with EtOAc, dried (Na₂SO₄), filtered and evaporated. Column chromatography 4% MeOH/CH₂Cl₂ and then 50% EtOAc/Hexanes gave pure (Z)-4-(3-(tert-butoxycarbonylamino)-1-(isoquinolin-6-ylamino)-1-oxopropan-2-yl)benzyl 7-((1R,2R,3R,5S)-2-((R)-5-phenyl-3-(triisopropylsilyloxy)pentyl)-3,5-bis(triisopropylsilyloxy)cyclopentyl)hept-5-enoate (5).

Preparation of (Z)-4-(3-(tert-butoxycarbonylamino)-1-(isoquinolin-6-ylamino)-1-oxopropan-2-yl)benzyl 7-((1R,2R,3R,5S)-3,5-dihydroxy-2-((R)-3-hydroxy-5-phenylpentyl)cyclopentyl)hept-5-enoate (6)

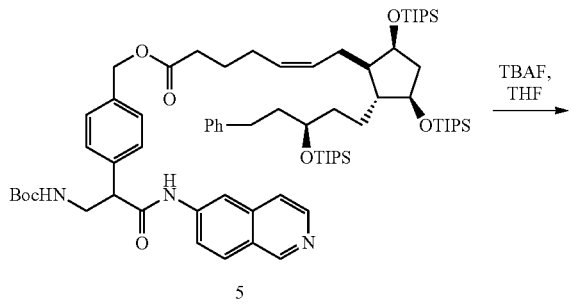

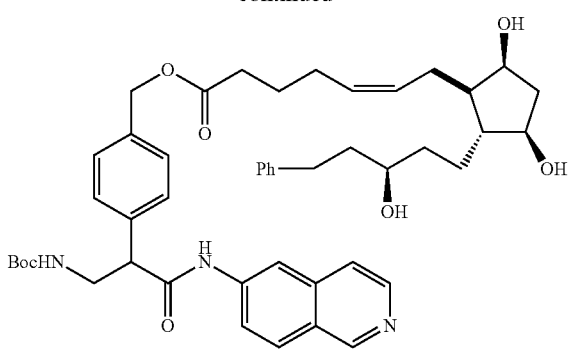

To 5 in THF cooled to 0° C. was added TBAF and the solution was stirred 5 min at 0° C. and 12 h at room temperature. The mixture was poured into NH₄Cl (sat)-EtOAc and extracted with EtOAc, dried (Na₂SO₄), filtered and evaporated. Column chromatography 5-8% MeOH/CH₂Cl₂ gave pure (Z)-4-(3-(tert-butoxycarbonylamino)-1-(isoquinolin-6-ylamino)-1-oxopropan-2-yl)benzyl 7-((1R,2R,3R,5S)-3,5-dihydroxy-2-((R)-3-hydroxy-5-phenylpentyl)cyclopentyl)hept-5-enoate (6).

Preparation of (Z)-4-(3-amino-1-(isoquinolin-6-ylamino)-1-oxopropan-2-yl)benzyl 7-((1R,2R,3R,5S)-3, 5-dihydroxy-2-((R)-3-hydroxy-5-phenylpentyl)cyclopentyl) hept-5-enoate dihydrochloride (7)

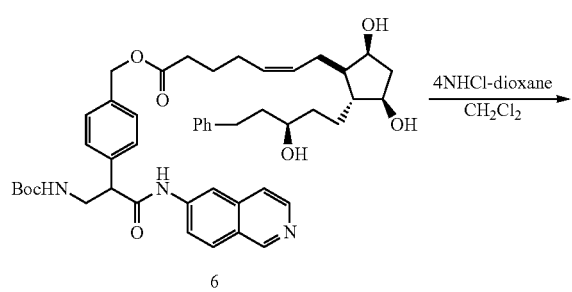

6

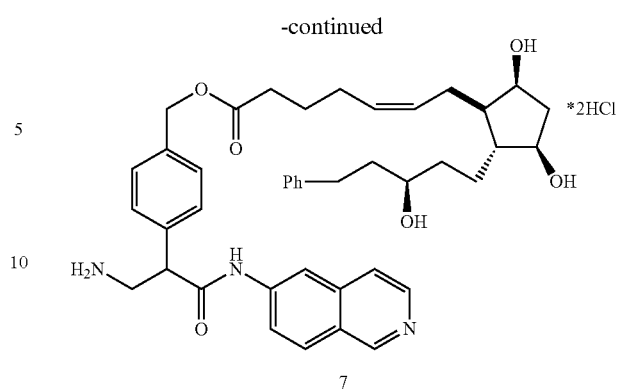

7

To 6 in CH$_2$Cl$_2$ was added HCl (4N in dioxane) and the solution was stirred for 2 hours at room temperature. The solvents were evaporated to give (Z)-4-(3-amino-1-(isoquinolin-6-ylamino)-1-oxopropan-2-yl)benzyl 7-((1R,2R,3R, 5S)-3,5-dihydroxy-2-((R)-3-hydroxy-5-phenylpentyl)cyclopentyl)hept-5-enoate dihydrochloride (7).

Example 8. Synthesis of ROCKi-Fluprostenol Conjugate

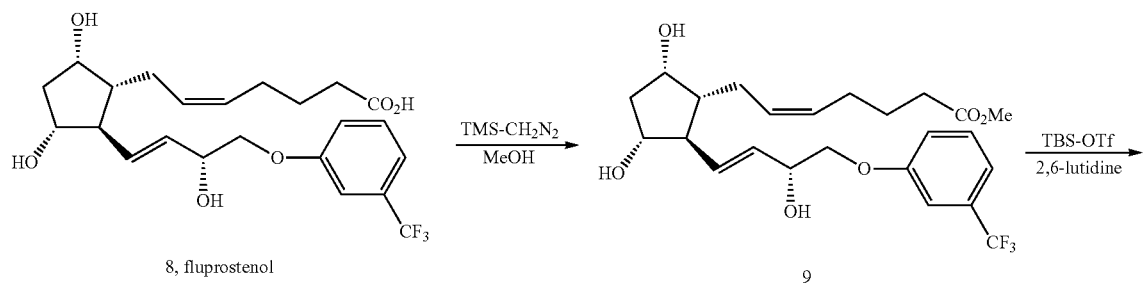

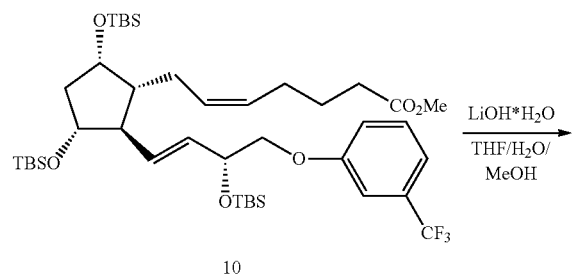

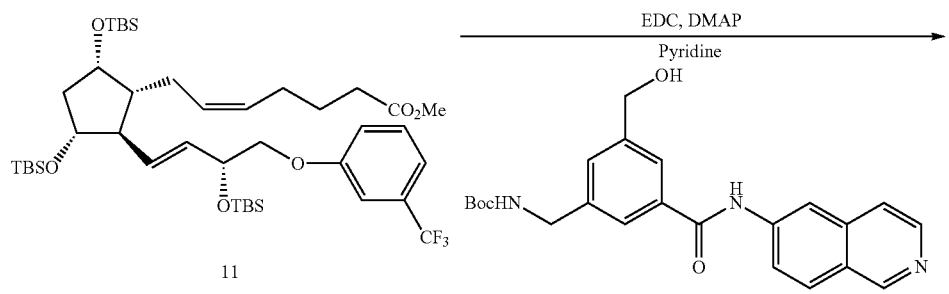

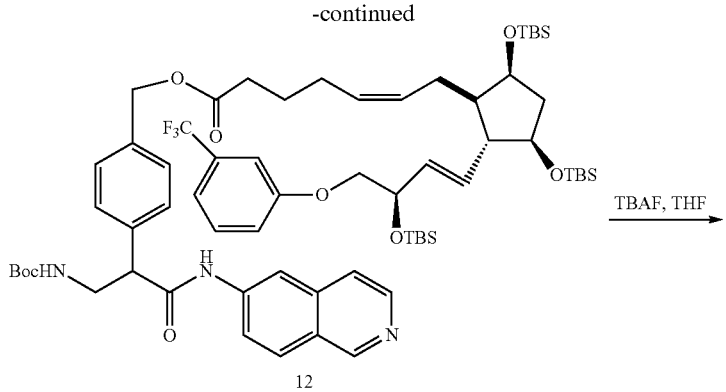

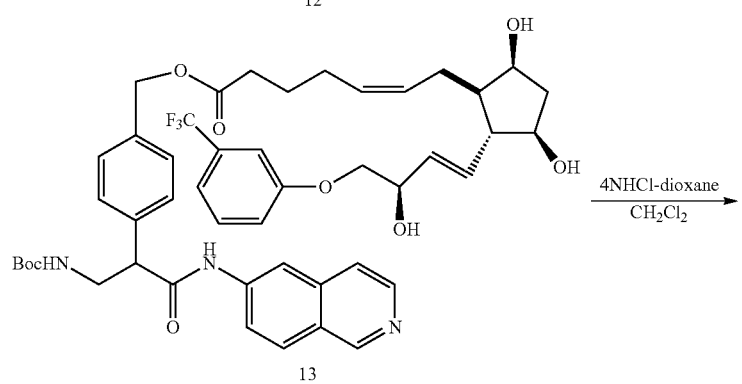

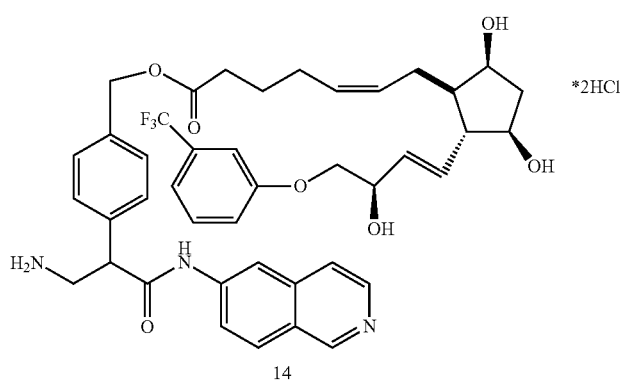

Preparation of (Z)-methyl 7-((1R,2R,3R,5S)-3,5-dihydroxy-2-((R,E)-3-hydroxy-4-(3-(trifluoromethyl)phenoxy)but-1-enyl)cyclopentyl)hept-5-enoate (9)

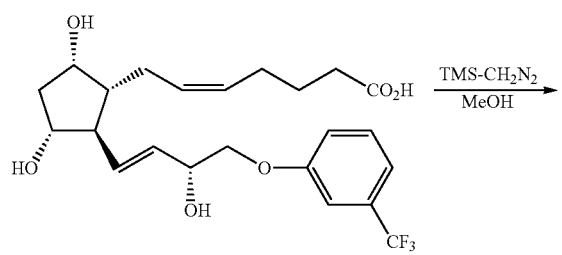

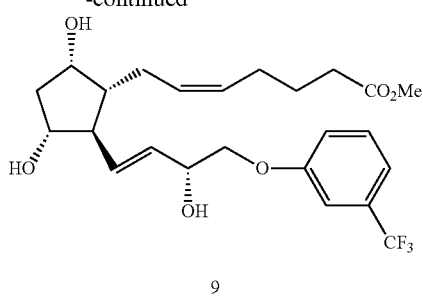

To fluprostenol in MeOH at 0° C. was added TMS-CH$_2$N$_2$ until the solution persisted a yellow color. AcOH (2 drops) were added to quench excess TMS-CH$_2$N$_2$ and the solvents were evaporated. Column chromatography 90%-100% EtOAc/Hexanes gave pure (Z)-methyl 7-((1R,2R,3R,5S)-3,5-dihydroxy-2-((R,E)-3-hydroxy-4-(3-(trifluoromethyl)phenoxy)but-1-enyl)cyclopentyl)hept-5-enoate (9).

Preparation of (Z)-methyl 7-((1R,2R,3R,5S)-3,5-bis (tert-butyldimethylsilyloxy)-2-((R,E)-3-(tert-butyldimethylsilyloxy)-4-(3-(trifluoromethyl)phenoxy)but-1-enyl)cyclopentyl)hept-5-enoate (10)

Preparation of (Z)-7-((1R,2R,3R,5S)-3,5-bis(tert-butyldimethylsilyloxy)-2-((R,E)-3-(tert-butyldimethylsilyloxy)-4-(3-(trifluoromethyl)phenoxy)but-1-enyl)cyclopentyl)hept-5-enoic acid (11)

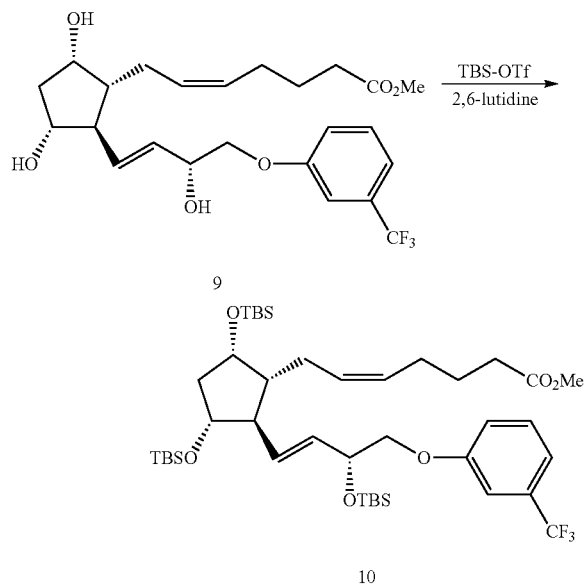

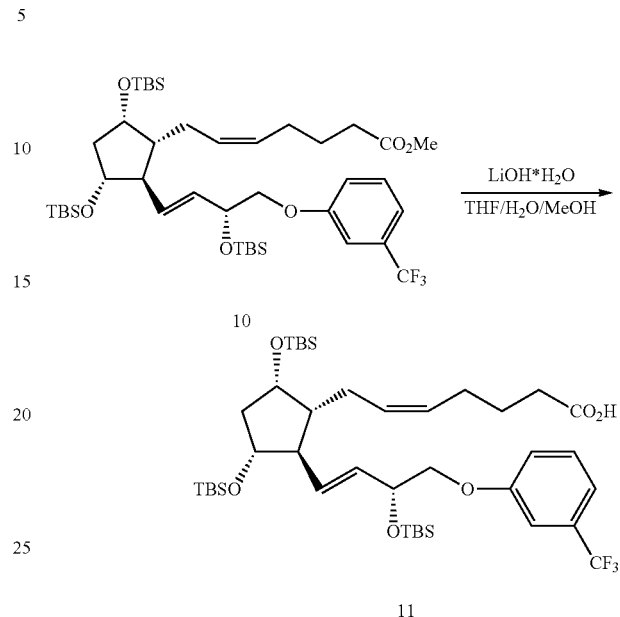

To (Z)-methyl 7-((1R,2R,3R,5S)-3,5-dihydroxy-2-((R,E)-3-hydroxy-4-(3-(trifluoromethyl)phenoxy)but-1-enyl)cyclopentyl)hept-5-enoate (9) in CH$_2$Cl$_2$ cooled to 0° C. was added 2,6-lutidine and TBS-OTf and solution was stirred for 30 min at 0° C. and then stirred for 12 hours at room temperature. The solution was poured into EtOAc and NH$_4$Cl(sat)/HCl (1 N) (3:1) and further extracted with EtOAc. The organics were dried (Na$_2$SO$_4$), filtered and evaporated. Column chromatography 10% EtOAc/Hexanes gave (Z)-methyl 7-((1R,2R,3R,5S)-3,5-bis(tert-butyldimethylsilyloxy)-2-((R,E)-3-(tert-butyldimethylsilyloxy)-4-(3-(trifluoromethyl)phenoxy)but-1-enyl)cyclopentyl)hept-5-enoate (10).

To 10 in THF/MeOH/H$_2$O was added LiOH*H$_2$O and the solution was stirred overnight at room temperature. The solution was poured into EtOAc and NH$_4$Cl(sat)/HCl (1 N) (3:1) and further extracted with EtOAc. The organics were dried (Na$_2$SO$_4$), filtered and evaporated. Column chromatography 10% EtOAc/Hexanes 1.5% AcOH gave pure (Z)-7-((1R,2R,3R,5S)-3,5-bis(tert-butyldimethylsilyloxy)-2-((R,E)-3-(tert-butyldimethylsilyloxy)-4-(3-(trifluoromethyl)phenoxy)but-1-enyl)cyclopentyl)hept-5-enoic acid (11).

Preparation of (Z)-4-(3-(tert-butoxycarbonylamino)-1-(isoquinolin-6-ylamino)-1-oxopropan-2-yl)benzyl 7-((1R,2R,3R,5S)-3,5-bis(tert-butyldimethylsilyloxy)-2-((R,E)-3-(tert-butyldimethylsilyloxy)-4-(3-(trifluoromethyl)phenoxy)but-1-enyl)cyclopentyl) hept-5-enoate (12)

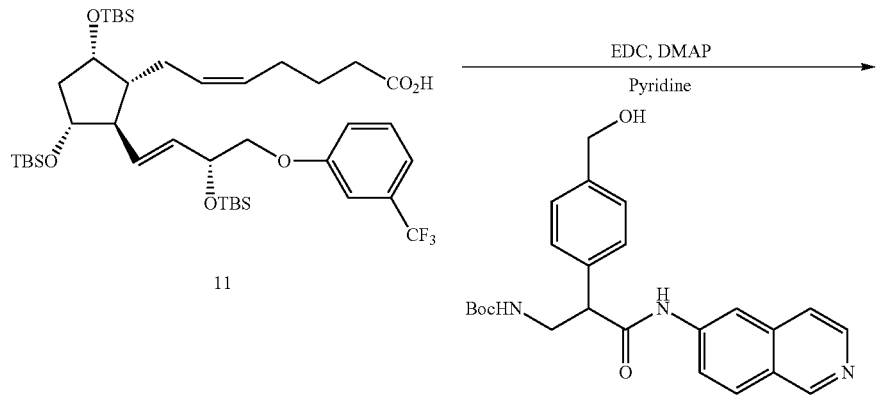

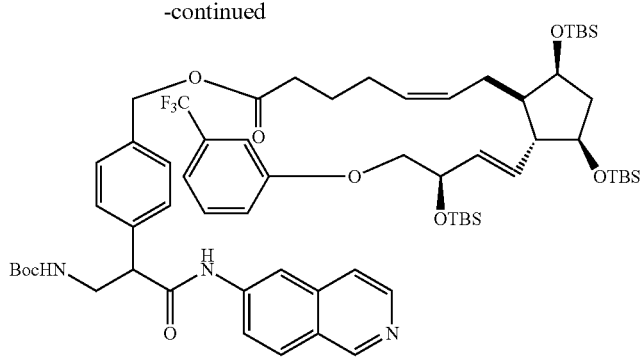

12

To 11 in pyridine was added tert-butyl 2-(4-(hydroxymethyl)phenyl)-3-(isoquinolin-6-ylamino)-3-oxopropylcarbamate, EDC, and DMAP and the solution was flushed with Argon, capped and stirred overnight. The mixture as poured into NaHCO$_3$(sat) and extracted with EtOAc, dried (Na$_2$SO$_4$), filtered and evaporated. Column chromatography 4% MeOH/CH$_2$Cl$_2$ gave pure (Z)-4-(3-(tert-butoxycarbonylamino)-1-(isoquinolin-6-ylamino)-1-oxopropan-2-yl)benzyl 7-((1R,2R,3R,5 S)-3,5-bis(tert-butyldimethyl silyloxy)-2-((R,E)-3-(tert-butyldimethylsilyloxy)-4-(3-(trifluoromethyl)phenoxy)but-1-enyl)cyclopentyl)hept-5-enoate (12).

Preparation of (Z)-4-(3-(tert-butoxycarbonylamino)-1-(isoquinolin-6-ylamino)-1-oxopropan-2-yl)benzyl 7-((1R,2R,3R,5S)-3,5-dihydroxy-2-((R,E)-3-hydroxy-4-(3-(trifluoromethyl)phenoxy)but-1-enyl)cyclopentyl)hept-5-enoate (13)

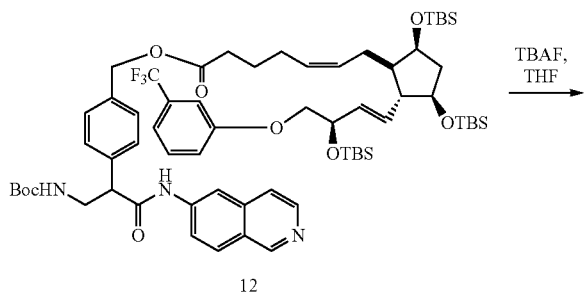

12

TBAF, THF →

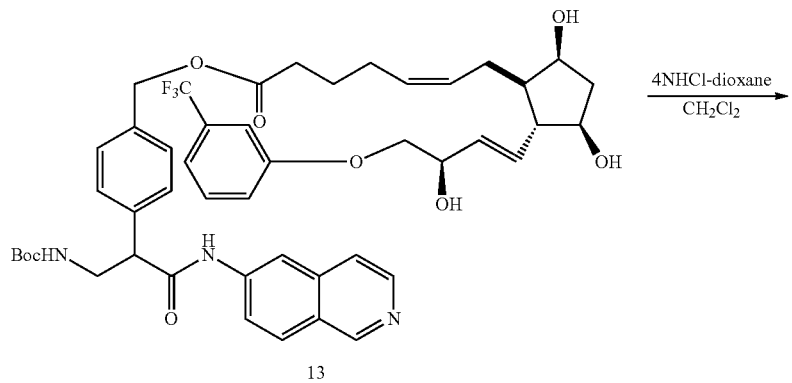

13

To 12 in THF cooled to 0° C. was added TBAF and the solution was stirred 5 min at 0° C. and 12 h at room temperature. The mixture was poured into NH$_4$Cl (sat)-EtOAc and extracted with EtOAc. The EtOAc layer was then washed with NH$_4$Cl(sat), dried (Na$_2$SO$_4$), filtered and evaporated. Column chromatography 5-10% MeOH/CH$_2$Cl$_2$ gave pure (Z)-4-(3-(tert-butoxycarbonylamino)-1-(isoquinolin-6-ylamino)-1-oxopropan-2-yl)benzyl 7-((1R,2R,3R,5S)-3,5-dihydroxy-2-((R,E)-3-hydroxy-4-(3-(trifluoromethyl)phenoxy)but-1-enyl)cyclopentyl)hept-5-enoate (13).

Preparation of (Z)-4-(3-amino-1-(isoquinolin-6-ylamino)-1-oxopropan-2-yl)benzyl 7-((1R,2R,3R,5S)-3,5-dihydroxy-2-((R,E)-3-hydroxy-4-(3-(trifluoromethyl)phenoxy)but-1-enyl)cyclopentyl)hept-5-enoate dihydrochloride (14)

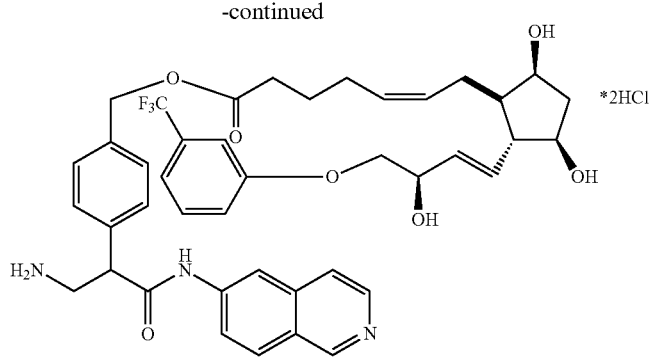

14

To 13 in CH$_2$Cl$_2$ was added HCl (4N in dioxane) and the solution was stirred for 2 hours at room temperature. The solvents were evaporated and column chromatography 10-20% MeOH/CH$_2$Cl$_2$ gave pure (Z)-4-(3-amino-1-(isoquinolin-6-ylamino)-1-oxopropan-2-yl)benzyl 7-((1R,2R,3R,5S)-3,5-dihydroxy-2-((R,E)-3-hydroxy-4-(3-(trifluoromethyl)phenoxy)but-1-enyl)cyclopentyl)hept-5-enoate dihydrochloride (14).

Example 9. Synthesis of ROCKi-AR-102 Free Acid Conjugate

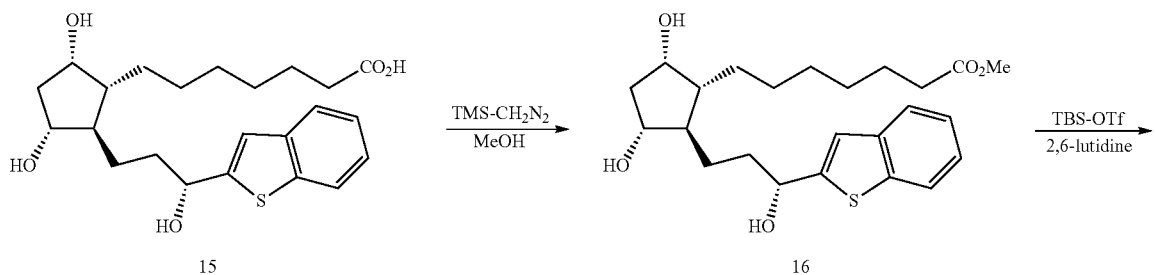

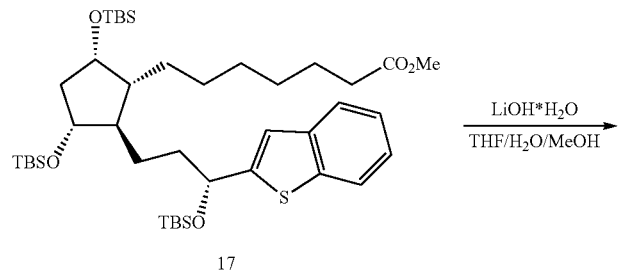

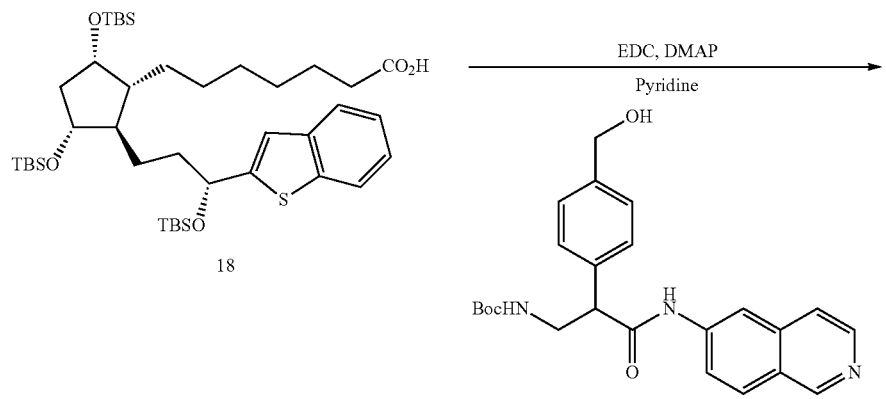

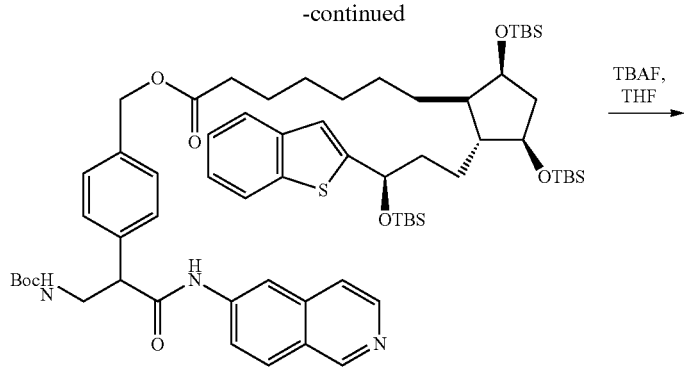
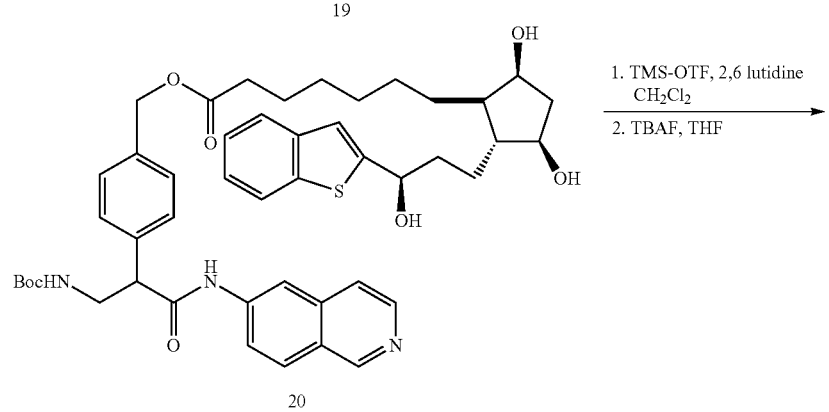
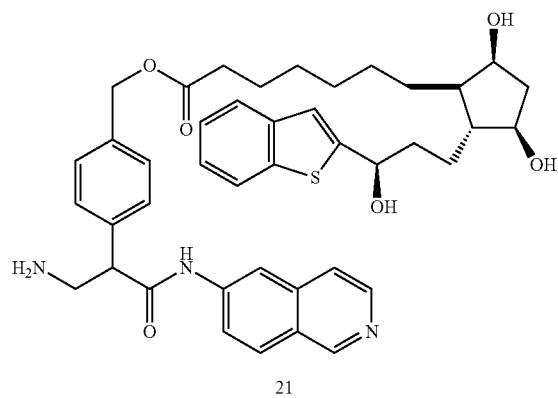
Preparation methyl 7-((1R,2R,3R,5S)-2-((R)-3-(benzo[b]thiophen-2-yl)-3-hydroxypropyl)-3,5-dihydroxycyclopentyl)heptanoate (16)
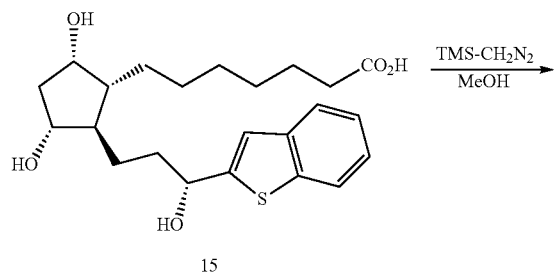
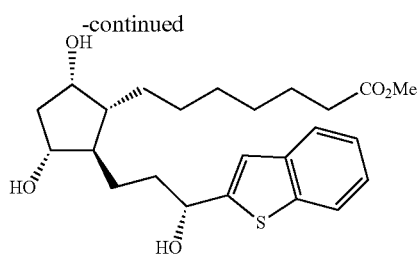
To AR-102 free acid (15) in MeOH at 0° C. was added TMS-CH$_2$N$_2$ until the solution persisted a yellow color. AcOH (2 drops) were added to quench excess TMS-CH$_2$N$_2$ and the solvents were evaporated. Column chromatography 90%-100% EtOAc/Hexanes gave pure methyl 7-((1R,2R, 3R,5S)-2-((R)-3-(benzo[b]thiophen-2-yl)-3-hydroxypropyl)-3,5-dihydroxycyclopentyl)heptanoate (16).

Preparation of methyl 7-((1R,2R,3R,5S)-2-((R)-3-(benzo[b]thiophen-2-yl)-3-(tert-butyldimethylsilyloxy)propyl)-3,5-bis(tert-butyldimethylsilyloxy)cyclopentyl)heptanoate (17)

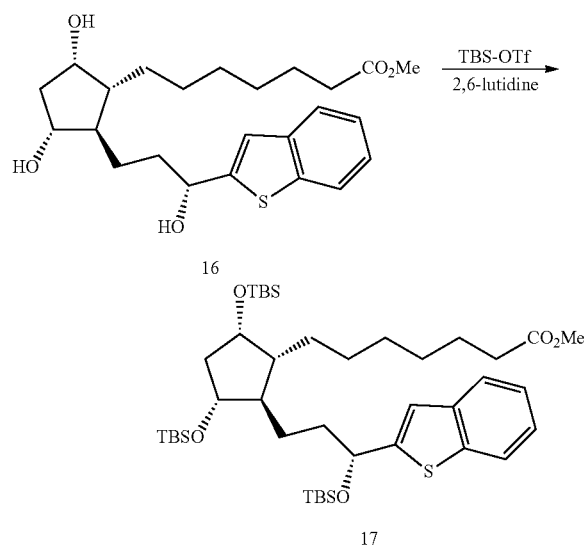

To (methyl 7-((1R,2R,3R,5S)-2-((R)-3-(benzo[b]thiophen-2-yl)-3-hydroxypropyl)-3,5-dihydroxycyclopentyl)heptanoate (16) in CH$_2$Cl$_2$ cooled to 0° C. was added 2,6-lutidine and TBS-OTf and solution was stirred for 30 min at 0° C. and then stirred for 12 hours at room temperature. The solution was poured into EtOAc and NH$_4$Cl(sat)/HCl (1 N) (3:1) and further extracted with EtOAc. The organics were dried (Na$_2$SO$_4$), filtered and evaporated. Column chromatography 10% EtOAc/Hexanes gave methyl 7-((1R,2R,3R,5S)-2-((R)-3-(benzo[b]thiophen-2-yl)-3-(tert-butyldimethylsilyloxy)propyl)-3,5-bis(tert-butyldimethylsilyloxy)cyclopentyl)heptanoate (17).

Preparation of 7-((1R,2R,3R,5S)-2-((R)-3-(benzo[b]thiophen-2-yl)-3-(tert-butyldimethylsilyloxy)propyl)-3,5-bis(tert-butyldimethylsilyloxy)cyclopentyl)heptanoic acid (18)

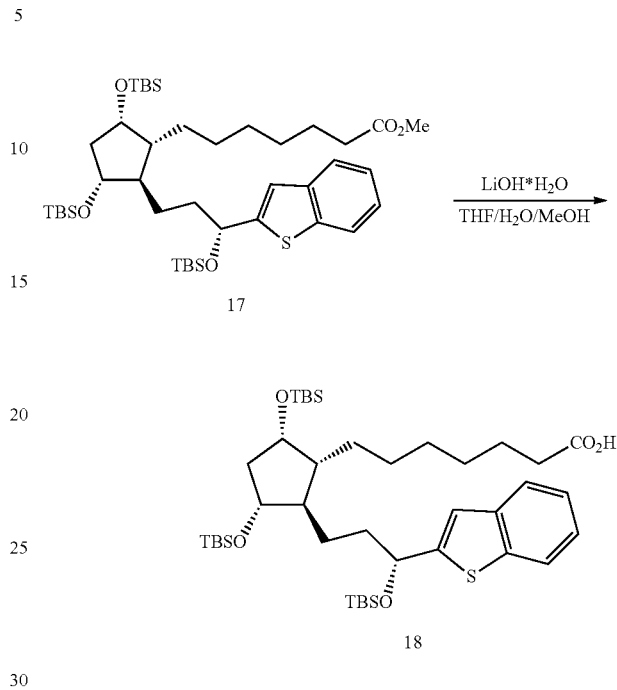

To 17 in THF/MeOH/H$_2$O was added LiOH*H$_2$O and the solution was stirred overnight at room temperature. The solution was poured into EtOAc and NH$_4$Cl(sat)/HCl (1 N) (3:1) and further extracted with EtOAc. The organics were dried (Na$_2$SO$_4$), filtered and evaporated. Column chromatography 10% EtOAc/Hexanes 1.5% AcOH gave pure 7-((1R,2R,3R,5S)-2-((R)-3-(benzo[b]thiophen-2-yl)-3-(tert-butyldimethylsilyloxy)propyl)-3,5-bis(tert-butyldimethylsilyloxy)cyclopentyl)heptanoic acid (18).

Preparation of 4-(3-(tert-butoxycarbonylamino)-1-(isoquinolin-6-ylamino)-1-oxopropan-2-yl)benzyl 7-((1R,2R,3R,5S)-2-((R)-3-(benzo[b]thiophen-2-yl)-3-(tert-butyldimethylsilyloxy)propyl)-3,5-bis(tert-butyldimethylsilyloxy)cyclopentyl)heptanoate (19)

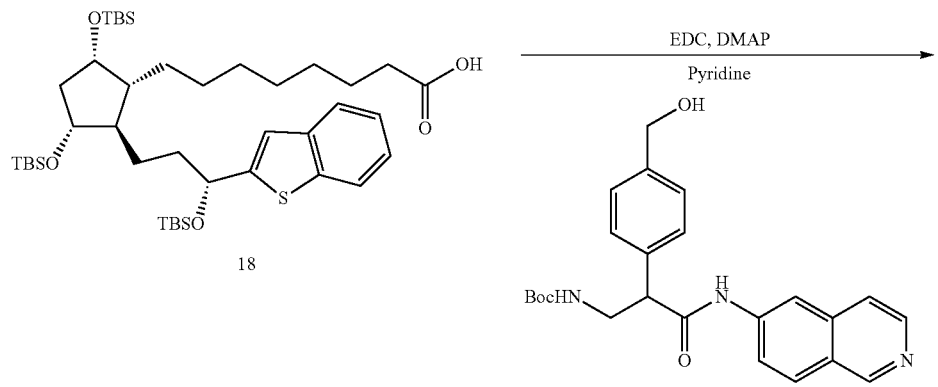

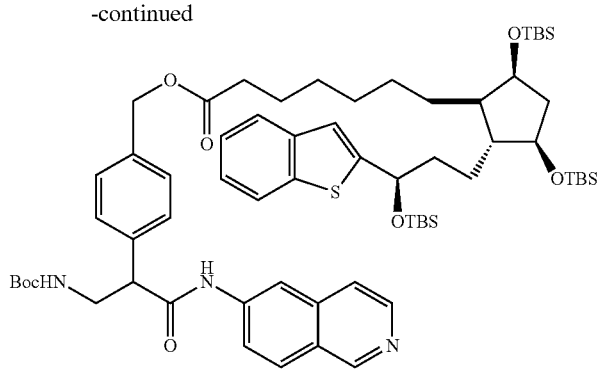

19

To 18 in pyridine was added tert-butyl 2-(4-(hydroxymethyl)phenyl)-3-(isoquinolin-6-ylamino)-3-oxopropylcarbamate, EDC, and DMAP and the solution was flushed with Argon, capped and stirred overnight. The mixture as poured into NaHCO₃(sat) and extracted with EtOAc, dried (Na₂SO₄), filtered and evaporated. Column chromatography 4% MeOH/CH₂Cl₂ gave pure 4-(3-(tert-butoxycarbonylamino)-1-(isoquinolin-6-ylamino)-1-oxopropan-2-yl) benzyl 7-((1R,2R,3R,5 S)-2-((R)-3-(benzo[b]thiophen-2-yl)-3-(tert-butyldimethylsilyloxy)propyl)-3,5-bis(tert-butyldimethyl silyloxy)cyclopentyl)heptanoate (19).

Preparation of give pure 4-(3-(tert-butoxycarbonylamino)-1-(isoquinolin-6-ylamino)-1-oxopropan-2-yl)benzyl 7-((1R,2R,3R,5S)-2-((R)-3-(benzo[b]thiophen-2-yl)-3-hydroxypropyl)-3,5-dihydroxycyclopentyl)heptanoate (20)

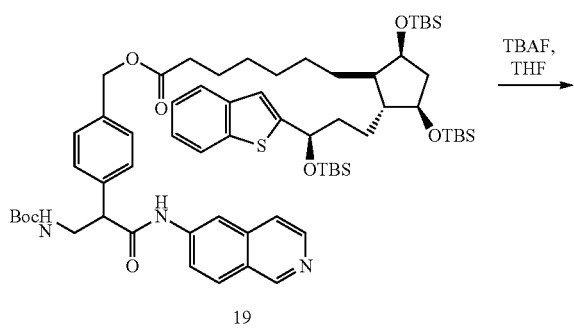

19

TBAF, THF →

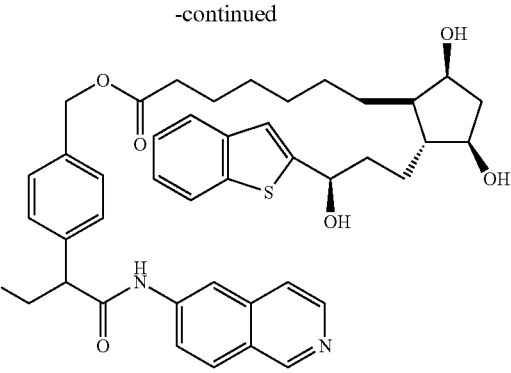

20

To 19 in THF cooled to 0° C. was added TBAF and the solution was stirred 5 min at 0° C. and 12 h at room temperature. The mixture was poured into NH₄Cl (sat)-EtOAc and extracted with EtOAc. The EtOAc layer was then washed with NH₄Cl(sat), dried (Na₂SO₄), filtered and evaporated. Column chromatography 5-10% MeOH/CH₂Cl₂ gave pure 4-(3-(tert-butoxycarbonylamino)-1-(isoquinolin-6-ylamino)-1-oxopropan-2-yl)benzyl 7-((1R,2R,3R,5S)-2-((R)-3-(benzo[b]thiophen-2-yl)-3-hydroxypropyl)-3,5-dihydroxycyclopentyl)heptanoate (20).

Preparation of 4-(3-amino-1-(isoquinolin-6-ylamino)-1-oxopropan-2-yl)benzyl 7-((1R,2R,3R,5S)-2-((R)-3-(benzo[b]thiophen-2-yl)-3-hydroxypropyl)-3,5-dihydroxycyclopentyl)heptanoate (21)

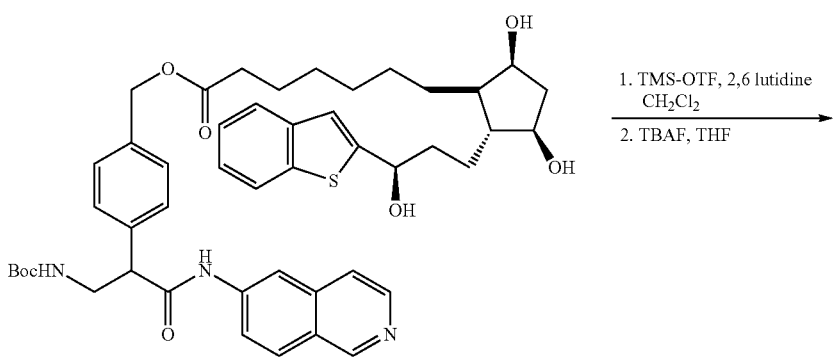

20

1. TMS-OTF, 2,6 lutidine CH₂Cl₂
2. TBAF, THF →

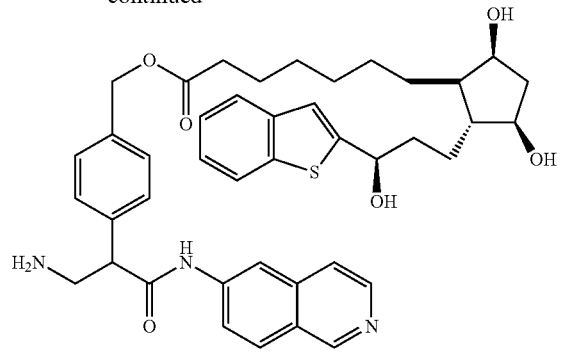

21

To 20 in CH₂Cl₂ was added 2,6 lutidine (11 eq) and TMS-OTF (11 eq) and the solution was stirred for 40 min at room temperature. The mixture was poured into NaHCO₃ (sat) and extracted with CH₂Cl₂. The organics were dried (Na₂SO₄), filtered and evaporated. To the crude mixture was added THF and TBAF (1 eq) and the solution was stirred at room temperature for 15 min. The mixture was poured into NaHCO₃ (sat) and extracted with CH₂Cl₂, dried (Na₂SO₄) filtered and evaporated. Column chromatography 20% MeOH/CH₂Cl₂ gave pure 4-(3-amino-1-(isoquinolin-6-ylamino)-1-oxopropan-2-yl)benzyl 7-((1R,2R,3R,5S)-2-((R)-3-(benzo[b]thiophen-2-yl)-3-hydroxypropyl)-3,5-dihydroxycyclopentyl)heptanoate (21).

Example 10. ROCKi-Prostaglandin Salts

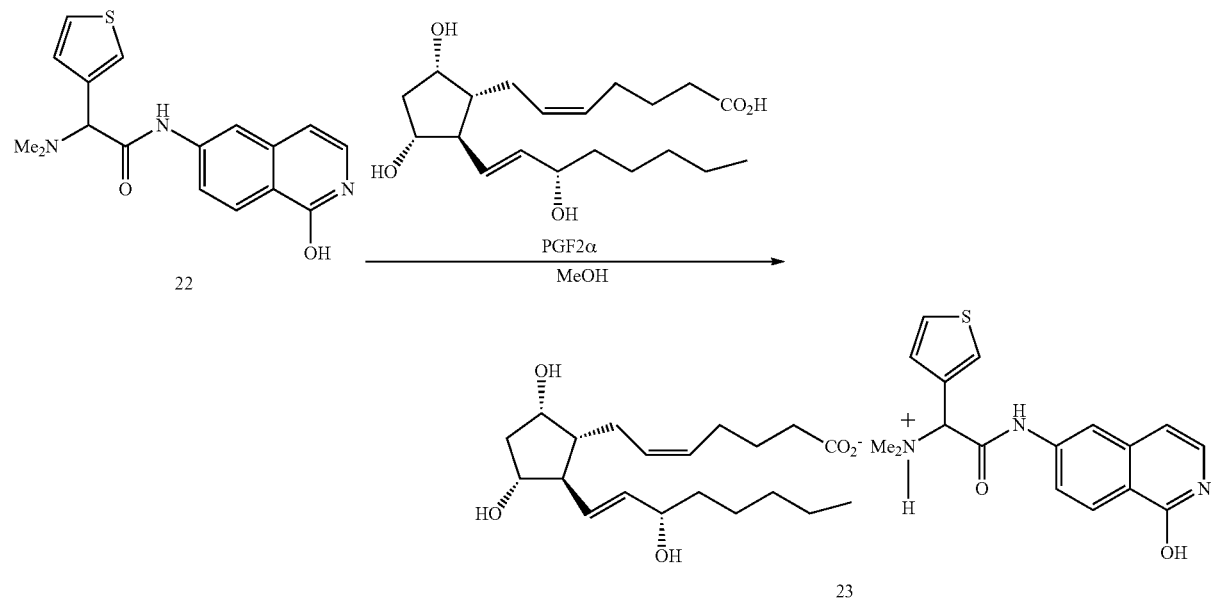

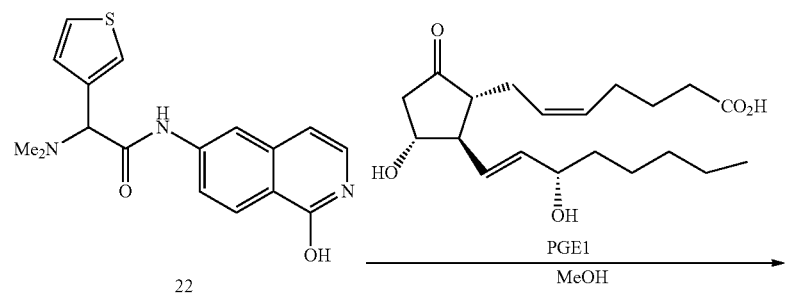

-continued
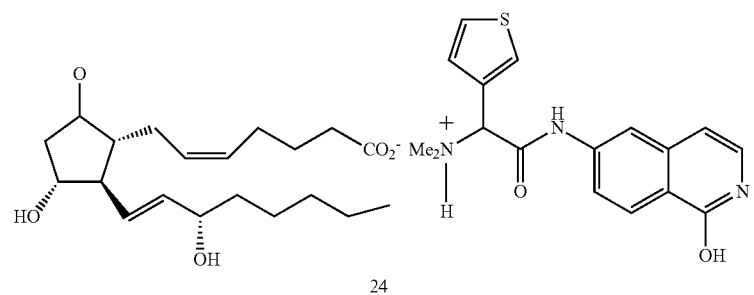
24
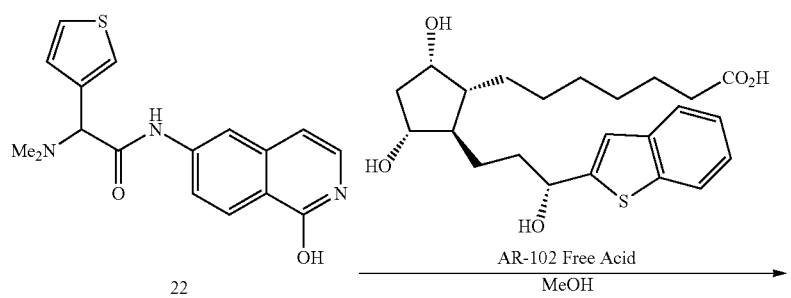
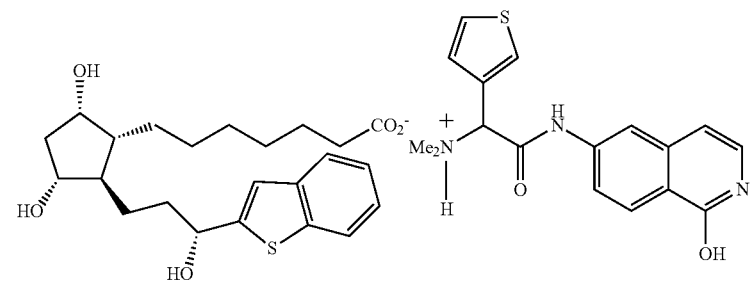
25
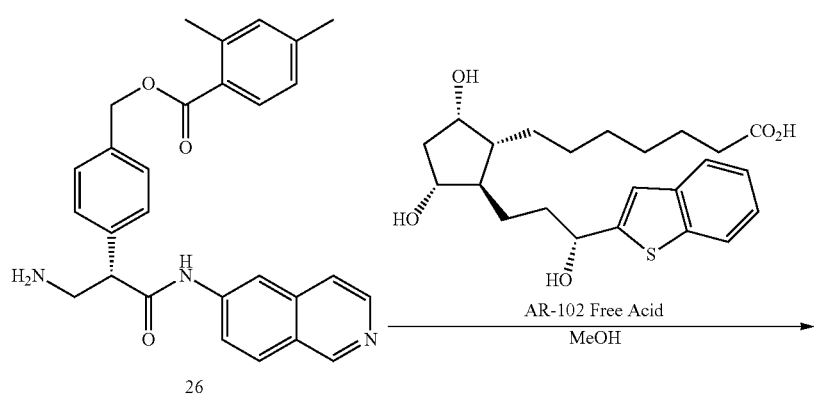

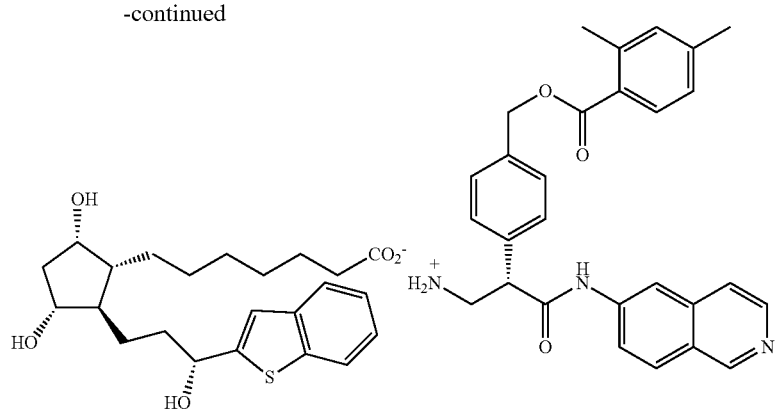

27

Preparation of the salt of 2-(dimethylamino)-N-(1-hydroxyisoquinolin-6-yl)-2-(thiophen-3-yl)acetamide and (Z)-7-((1R,2R,3R,5S)-3,5-dihydroxy-2-((S,E)-3-hydroxyoct-1-enyl)cyclopentyl)hept-5-enoic acid (PGF2α) (23)

To 22 in MeOH was added PGF$_{2\alpha}$ and the solution was heated to 70° C. to dissolve. The solvents were evaporated to give salt 23.

Salts 24 and 25 were prepared similarly to salt 23. Salt 27 was prepared from 26 following the same method, but without heat.

While the disclosure has been described in detail and with reference to specific embodiments thereof, it will be apparent to one skilled in the art that various changes and modifications can be made without departing from the spirit and scope of the disclosure.

The invention claimed is:

1. A compound according to formula (II):

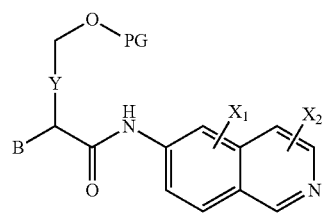

(II)

or a pharmaceutically acceptable salt thereof, wherein:
Y is phenylene;
B is —NR$_1$R$_2$ or —CH$_2$NR$_1$R$_2$;
R$_1$ and R$_2$ are each independently hydrogen or C$_1$-C$_4$ alkyl;
X$_1$ and X$_2$ are hydrogen; and
PG is an acyl radical of latanoprost, bimatoprost, travoprost, tafluprost, AR-102, cloprostenol, unoprostone, or PGF$_{2\alpha}$.

2. The compound of claim 1, wherein:
B is —CH$_2$NR$_1$R$_2$; and
R$_1$ and R$_2$ are hydrogen.

3. The compound of claim 1, wherein PG is an acyl radical of latanoprost.

4. The compound of claim 1, wherein PG is an acyl radical of AR-102.

5. The compound of claim 1, wherein PG is an acyl radical of bimatoprost.

6. A composition comprising a compound of claim 1, and at least one of a buffer, a chelating agent, a tonicity agent, a preservative, a viscosity enhancer, a sugar or a sugar alcohol, or a surfactant.

7. The compound of claim 1, wherein PG is an acyl radical of travoprost.

8. A method of treating glaucoma in a subject in need thereof, comprising administering to the subject a compound of claim 1.

9. The method of claim 8, wherein the compound is administered topically to an eye of the subject.

10. A method of reducing intraocular pressure in a subject in need thereof, comprising topically administering to an eye of the subject a compound of claim 1.

11. A compound, wherein the compound is:

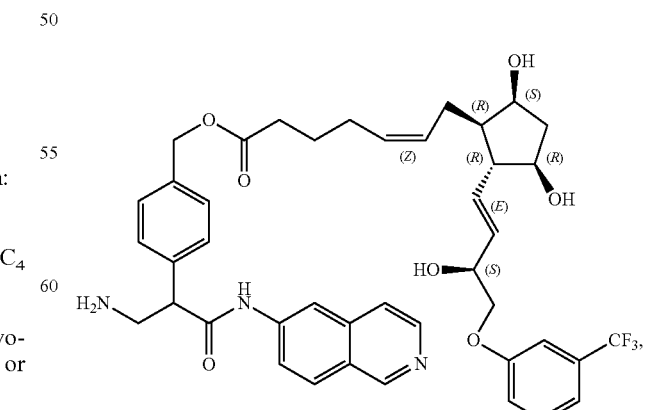

-continued

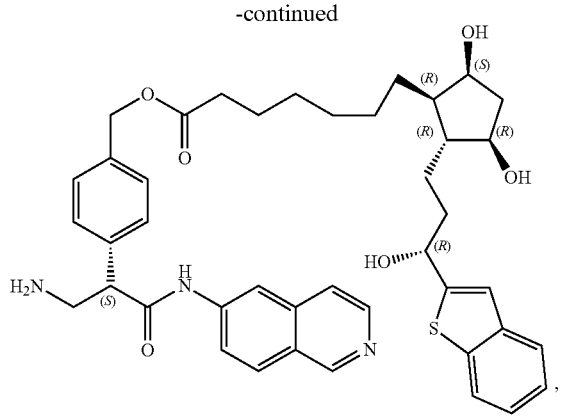

or a pharmaceutically acceptable salt thereof.

12. A composition comprising a compound of claim 11, further comprising at least one of a buffer, a chelating agent, a tonicity agent, a preservative, a viscosity enhancer, a sugar or a sugar alcohol, or a surfactant.

13. A method of treating glaucoma in a subject in need thereof, comprising administering to the subject a compound of claim 11.

14. The method of claim 13, wherein the compound is administered topically to an eye of the subject.

15. A method of reducing intraocular pressure in a subject in need thereof, comprising topically administering to an eye of the subject a compound of claim 11.

16. A compound according to formula (II):

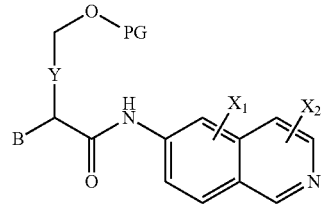

(II)

or a pharmaceutically acceptable salt thereof;
wherein
Y is phenylene;
B is —$CH_2NR_1R_2$;
$R_1$ and $R_2$ are hydrogen;
$X_1$ and $X_2$ are hydrogen; and
PG is an acyl radical of latanoprost.

17. A composition comprising a compound of claim 16, further comprising at least one of a buffer, a chelating agent, a tonicity agent, a preservative, a viscosity enhancer, a sugar or a sugar alcohol, or a surfactant.

18. A method of treating glaucoma in a subject in need thereof, comprising administering to the subject a compound of claim 16.

19. The method of claim 18, wherein the compound is administered topically to an eye of the subject.

20. A method of reducing intraocular pressure in a subject in need thereof, comprising topically administering to an eye of the subject a compound of claim 16.

21. The compound of claim 2, wherein PG is an acyl radical of bimatoprost.

* * * * *